US009199987B2

(12) United States Patent
Wolkerstorfer et al.

(10) Patent No.: US 9,199,987 B2
(45) Date of Patent: Dec. 1, 2015

(54) SUBSTITUTED NAPHTHYRIDINES FOR THE TREATMENT, AMELIORATION OR PREVENTION OF A VIRAL DISEASE

(71) Applicants: Savira pharmaceuticals GmbH, Vienna (AT); European Molecular Biology Laboratory, Heidelberg (DE); F. Hoffman-La Roche AG, Basel (CH)

(72) Inventors: Andrea Wolkerstorfer, Vienna (AT); Oliver Szolar, Vienna (AT); Norbert Handler, Vienna (AT); Helmut Buschmann, Aachen (DE); Stephen Cusack, Seyssinet-Pariset (FR); Mark Smith, Jersey City, NJ (US); Sung-Sau So, Verona, NJ (US); Ronald Charles Hawley, San Francisco, CA (US); Achyutharao Sidduri, Newark, NJ (US)

(73) Assignees: Savira pharmaceuticals GmbH, Vienna (AU); European Molecular Biology Laboratory, Heidelberg (DE); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 14/149,381

(22) Filed: Jan. 7, 2014

(65) Prior Publication Data
US 2014/0194432 A1 Jul. 10, 2014

Related U.S. Application Data

(60) Provisional application No. 61/750,032, filed on Jan. 8, 2013.

(51) Int. Cl.
| | |
|---|---|
| A61K 31/4375 | (2006.01) |
| C07D 221/04 | (2006.01) |
| C07D 471/04 | (2006.01) |
| A61K 31/4985 | (2006.01) |
| A61K 45/06 | (2006.01) |

(52) U.S. Cl.
CPC .......... *C07D 471/04* (2013.01); *A61K 31/4375* (2013.01); *A61K 31/4985* (2013.01); *A61K 45/06* (2013.01)

(58) Field of Classification Search
CPC .................. A61K 31/4375; C07D 221/04
USPC ........................... 514/300; 546/122
See application file for complete search history.

(56) References Cited

FOREIGN PATENT DOCUMENTS

| WO | WO0204444 A2 | 1/2002 |
| WO | WO2009089263 A2 | 7/2009 |
| WO | WO2011041143 A1 | 4/2011 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Chawla, et al. Current Research & Information on Pharmaceutical Sciences (CRIPS), 5(1), 2004, 9-12.*
Wolff, Manfred E., Ed. Burger's Medicinal Chemistry and Drug Discovery—Fifth Edition, New York: John Wiley & Sons, 1, 1996, 975-976.*
Kuduk et al., "Heterocyclic Fused Pyridone Carboxylic Acid M1 Positive Allosteric Modulators," Bioorganic & Medicinal Chemistry Letters, 20, pp. 2533-2537 (2010).
Gewald et al., "Synthesis and Structure-Activity Relationship Studies of Dihydronaphthyridinediones as a Novel Structural Class of Potent and Selective PDE7 Inhibitors," Bioorganic & Medicinal Chemistry Letters, 21, pp. 6652-6656 (2011).

* cited by examiner

*Primary Examiner* — Douglas M Willis
(74) *Attorney, Agent, or Firm* — Bryan Cave LLP

(57) ABSTRACT

The present invention relates to a compound having the general formula (V), optionally in the form of a pharmaceutically acceptable salt, solvate, polymorph, codrug, cocrystal, prodrug, tautomer, racemate, enantiomer, or diastereomer or mixture thereof, (V)

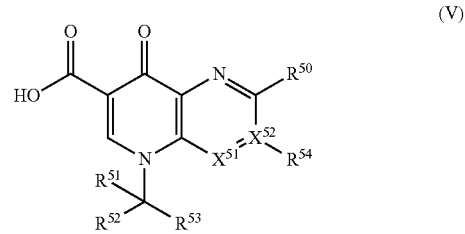

which are useful in treating, ameliorating or preventing a viral disease. Furthermore, specific combination therapies are disclosed.

8 Claims, No Drawings

SUBSTITUTED NAPHTHYRIDINES FOR THE TREATMENT, AMELIORATION OR PREVENTION OF A VIRAL DISEASE

CROSS REFERENCE TO RELATED APPLICATIONS

This application claims priority to U.S. Provisional Application No. 61/750,032, filed Jan. 8, 2013.

FIELD OF THE INVENTION

The present invention relates to a compound having the general formula (V), optionally in the form of a pharmaceutically acceptable salt, solvate, polymorph, codrug, cocrystal, prodrug, tautomer, racemate, enantiomer, or diastereomer or mixture thereof, $$\text{(V)}$$

which is useful in treating, ameloriating or preventing a viral disease. Furthermore, specific combination therapies are disclosed.

BACKGROUND OF THE INVENTION

In recent years the serious threat posed by influenza virus infection to worldwide public health has been highlighted by, firstly, the ongoing level transmission to humans of the highly pathogenic avian influenza A virus H5N1 strain (63% mortality in infected humans, http://www.who.int/csr/disease/avian_influenza/en/) and secondly, the unexpected emergence in 2009 of a novel pandemic influenza virus strain A/H1N1 that has rapidly spread around the entire world (http://www.who.int/csr/disease/swineflu/en/). Whilst the new virus strain is highly contagious but currently generally results in relatively mild illness, the future evolution of this virus is unpredictable. In a much more serious, but highly plausible scenario, H5N1 and related highly pathogenic avian influenza viruses could acquire mutations rendering them more easily transmissible between humans or the new A/H1N1 could become more virulent and only a single point mutation would be enough to confer resistance to oseltamivir (Neumann et al., Nature, 2009 (18; 459(7249) 931-939)); as many seasonal H1N1 strains have recently done (Dharan et al., The Journal of the American Medical Association, 2009 Mar. 11; 301 (10), 1034-1041; Moscona et al., The New England Journal of Medicine, 2009 (March 5; 360(10) pp 953-956)). In this case, the delay in generating and deploying a vaccine (~6 months in the relatively favourable case of A/H1N1 and still not a solved problem for H5N1) could have been catastrophically costly in human lives and societal disruption.

It is widely accepted that to bridge the period before a new vaccine is available and to treat severe cases, as well as to counter the problem of viral resistance, a wider choice of anti-influenza drugs is required. Development of new anti-influenza drugs has therefore again become high priority, having been largely abandoned by the major pharmaceutical companies once the neuraminidase inhibitors became available.

An excellent starting point for the development of antiviral medication is structural data of essential viral proteins. Thus, the crystal structure determination of e.g. the influenza virus surface antigen neuraminidase (Von Itzstein, M. et al., (1993), Nature, 363, pp. 418-423) led directly to the development of neuraminidase inhibitors with antiviral activity preventing the release of virus from the cells, however, not the virus production itself. These and their derivatives have subsequently developed into the anti-influenza drugs, zanamivir (Glaxo) and oseltamivir (Roche), which are currently being stockpiled by many countries as a first line of defense against a possible pandemic. However, these medicaments only provide a reduction in the duration of the clinical disease. Alternatively, adamantanes, the other class of licensed anti-influenza drugs (e.g. amantadine and rimantadine) target the viral M2 ion channel protein, which is located in the viral membrane interfering with the uncoating of the virus particle inside the cell. However, they have not been extensively used due to their side effects and the rapid development of resistant virus mutants (Magden, J. et al., (2005), Appl. Microbiol. Biotechnol., 66, pp. 612-621). In addition, more unspecific viral drugs, such as ribavirin, have been shown to work for treatment of influenza and other virus infections (Eriksson, B. et al., (1977), Antimicrob. Agents Chemother., 11, pp. 946-951). However, ribavirin is only approved in a few countries, probably due to severe side effects (Furuta et al., ANTIMICROBIAL AGENTS AND CHEMOTHERAPY, 2005, p. 981-986). Clearly, new antiviral compounds are needed, preferably directed against different targets.

Influenza virus as well as Thogotovirus and isavirus belong to the family of Orthomyxoviridae which, as well as the family of the Bunyaviridae, including the Hantavirus, Nairovirus, Orthobunyavirus, and Phlebovirus, amongst others, are negative stranded RNA viruses. Their genome is segmented and comes in ribonucleoprotein particles that include the RNA dependent RNA polymerase which carries out (i) the initial copying of the single-stranded negative-sense viral RNA (vRNA) into viral mRNAs (i.e. transcription) and (ii) the vRNA replication. This enzyme, a trimeric complex composed of subunits PA, PB1 and PB2, is central to the life cycle of the virus since it is responsible for the replication and transcription of viral RNA. In previous work the atomic structure of two key domains of the polymerase, the mRNA cap-binding domain in the PB2 subunit (Guilligay et al., Nature Structural & Molecular Biology 2008; May; 15(5): 500-506) and the endonuclease-active site residing within the PA subunit (Dias et al., Nature 2009, 458, 914-918) have been identified and their molecular architecture has been characterized. These two sites are critical for the unique "cap-snatching" mode used to initiate mRNA transcription that is used by the influenza virus and certain other virus families of this genus to generate viral mRNAs. A 5' cap is a modified guanine nucleotide that has been added to the 5' end of a messenger RNA. The 5' cap (also termed an RNA cap or RNA m7G cap) consists of a terminal 7-methylguanosine residue which is linked through a 5'-5'-triphosphate bond to the first transcribed nucleotide. The viral polymerase binds to the 5' RNA cap of cellular mRNA molecules and cleaves the RNA cap together with a stretch of 10 to 15 nucleotides. The capped RNA fragments then serve as primers for the synthesis of viral mRNA (Plotch, S. J. et al., (1981), Cell, 23, pp. 847-858; Kukkonen, S. K. et al (2005), Arch. Virol., 150, pp. 533-556; Leahy, M. B. et al., (2005), J. Virol., 71, pp. 8347-8351; Noah, D. L. et al., (2005), Adv. Virus Res., 65, pp. 121-145).

The polymerase complex seems to be an appropriate antiviral drug target since it is essential for synthesis of viral mRNA and viral replication and contains several functional active sites likely to be significantly different from those found in host cell proteins (Magden, J. et al., (2005), Appl. Microbiol. Biotechnol., 66, pp. 612-621). Thus, for example, there have been attempts to interfere with the assembly of polymerase subunits by a 25-amino-acid peptide resembling the PA-binding domain within PB1 (Ghanem, A. et al., (2007), J. Virol., 81, pp. 7801-7804). Furthermore, the endonuclease activity of the polymerase has been targeted and a series of 4-substituted 2,4-dioxobutanoic acid compounds has been identified as selective inhibitors of this activity in influenza viruses (Tomassini, J. et al., (1994), Antimicrob. Agents Chemother., 38, pp. 2827-2837). In addition, flutimide, a substituted 2,6-diketopiperazine, identified in extracts of *Delitschia confertaspora*, a fungal species, has been shown to inhibit the endonuclease of influenza virus (Tomassini, J. et al., (1996), Antimicrob. Agents Chemother., 40, pp. 1189-1193). Moreover, there have been attempts to interfere with viral transcription by nucleoside analogs, such as 2'-deoxy-2'-fluoroguanosine (Tisdale, M. et al., (1995), Antimicrob. Agents Chemother., 39, pp. 2454-2458).

In Example 1 of WO 2011/041143, ethyl 4-oxo-1-{[4-(1H-pyrazolo-1-yl)phenyl]methyl}-1,4-dihydro-1,5-naphthyridine-3-carboxylate is disclosed as a synthesis intermediate.

Scott D. Kuduk et al., *Bioorganic & Medicinal Chemistry Letters*, 20 (2010) 2533-2537 describe certain heterocyclic fused pyridone carboxylic acid $M_1$ positive allosteric modulators.

It is an object of the present invention to identify further compounds which are effective against viral diseases and which have improved pharmacological properties.

BRIEF SUMMARY OF THE INVENTION

Accordingly, in a first embodiment, the present invention provides a compound having the general formula (V).

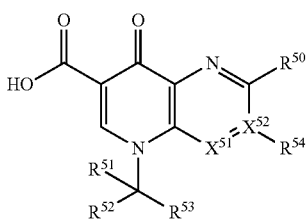

It is understood that throughout the present specification the term "a compound having the general formula (V)" encompasses pharmaceutically acceptable salts, solvates, polymorphs, prodrugs, codrugs, cocrystals, tautomers, racemates, enantiomers, or diastereomers or mixtures thereof unless mentioned otherwise.

A further embodiment of the present invention relates to a pharmaceutical composition comprising a compound having the general formula (V) and optionally one or more pharmaceutically acceptable excipient(s) and/or carrier(s).

The compounds having the general formula (V) are useful for treating, ameliorating or preventing viral diseases.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

The term "alkyl" refers to a saturated straight or branched carbon chain.

The term "cycloalkyl" represents a cyclic version of "alkyl". The term "cycloalkyl" is also meant to include bicyclic, tricyclic and polycyclic versions thereof. Unless specified otherwise, the cycloalkyl group can have 3 to 12 carbon atoms.

"Hal" or "halogen" represents F, Cl, Br and I.

"3- to 7-membered carbo- or heterocyclic ring" refers to a three-, four-, five-, six- or seven-membered ring wherein none, one or more of the carbon atoms in the ring have been replaced by 1 or 2 (for the three-membered ring), 1, 2 or 3 (for the four-membered ring) 1, 2, 3, or 4 (for the five-membered ring) or 1, 2, 3, 4, or 5 (for the six-membered ring) and 1, 2, 3, 4, 5 or 6 (for the seven-membered ring) of the same or different heteroatoms, whereby the heteroatoms are selected from O, N and S.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl, preferably phenyl.

The term "heteroaryl" preferably refers to a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from O, N and S. Examples of the heteroaryl group include pyrrole, pyrrolidine, oxolane, furan, imidazolidine, imidazole, pyrazole, oxazolidine, oxazole, thiazole, piperidine, pyridine, morpholine, piperazine, and dioxolane.

The term "hydrocarbon group which contains from 5 to 20 carbon atoms and optionally 1 to 4 heteroatoms selected from O, N and S and which contains at least one ring" refers to any group having 5 to 20 carbon atoms and optionally 1 to 4 heteroatoms selected from O, N and 2 as long as the group contains at least one ring. The term is also meant to include bicyclic, tricyclic and polycyclic versions thereof. If more than one ring is present, they can be separate from each other or be annelated. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —$(CH_2)_p$— with p=1 to 6). Examples of these groups include -(optionally substituted $C_{3-7}$ cycloalkyl), -(optionally substituted aryl) wherein the aryl group can be, for example, phenyl, -(optionally substituted biphenyl), adamantyl, —($C_{3-7}$ cycloalkyl)-aryl as well as the corresponding compounds with a linker.

If a compound or moiety is referred to as being "optionally substituted", it can in each instance include 1 or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichiometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups. Preferred examples of the prodrug include compounds in which COOH is replaced by C(O)OR or C(O)NRR;

wherein R is selected from H, $C_{5-10}$aryl, $C_{1-6}$alkyl-$C_{5-10}$aryl, $C_{1-6}$alkyl, $C_{1-6}$alkyl(—O—$C_{1-6}$alkyl)$_n$ (with n=1 to 30), $C_{1-6}$alkyl-C(O)OR, and $C_{5-10}$aryl-C(O)OR.

Compounds Having the General Formula (V)

The present invention provides a compound having the general formula (V).

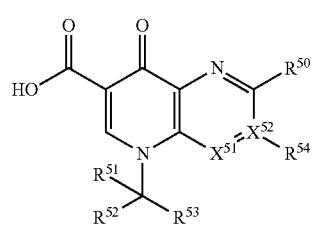

(V)

In the appended claims certain provisos are recited. It is understood that any of the compounds which are included in any of the provisos can be excluded, either individually or in combination with other compounds, from one or more of the independent claims having a different category even if it is not currently disclaimed in the independent claim of this category. It is also understood that the disclaimer covers the compounds in the form of their pharmaceutically acceptable salts, solvates, polymorphs, tautomers, racemates, enantiomers, and diastereomers.

The present invention provides a compound having the general formula (V) in which the following definitions apply.

$X^{51}$ is CH or N. In one embodiment, $X^{51}$ is CH. In another embodiment $X^{51}$ is N.

$X^{52}$—$R^{54}$ is N or C—$R^{57}$. In one embodiment, $X^{52}$—$R^{54}$ is N. In another embodiment $X^{52}$—$R^{54}$ is C—$R^{57}$.

$X^{53}$ is $NR^{55}$, $N(R^{55})C(O)$, $C(O)NR^{55}$, O, C(O), C(O)O, OC(O); $N(R^{55})SO_2$, $SO_2N(R^{55})$, S, SO, or $SO_2$; preferably $X^{53}$ is $NR^{55}$ or $N(R^{55})SO_2$; more preferably $NR^{55}$.

$R^{50}$ is —H, -(optionally substituted $C_{1-6}$ alkyl), -(optionally substituted $C_{3-7}$ cycloalkyl),-(optionally substituted aryl), —$C_{1-4}$ alkyl-(optionally substituted $C_{3-7}$ cycloalkyl), or —$C_{1-4}$ alkyl-(optionally substituted aryl); preferably $R^{50}$ is —H, or -(optionally substituted $C_{1-6}$ alkyl).

$R^{51}$ is —H, a —$C_{1-6}$ alkyl group, or a —$C_{1-6}$ alkyl group which is substituted by one or more halogen atoms; preferably $R^{51}$ is —H.

$R^{52}$ is —H, a —$C_{1-6}$ alkyl group, or a —$C_{1-6}$ alkyl group which is substituted by one or more halogen atoms; preferably $R^{52}$ is —H.

In one embodiment $R^{51}$ and $R^{52}$ can be joined together to form a 3- to 7-membered carbo- or heterocyclic ring.

$R^{53}$ is —$R^{56}$, or —$X^{53}$—$R^{56}$. In one embodiment $R^{53}$ is —$R^{56}$. In an alternative embodiment, $R^{53}$ is —$X^{50}$—$R^{56}$.

$R^{55}$ is —H, -(optionally substituted $C_{1-6}$ alkyl), -(optionally substituted $C_{3-7}$ cycloalkyl),-(optionally substituted aryl), —$C_{1-4}$ alkyl-(optionally substituted $C_{3-7}$ cycloalkyl), or —$C_{1-4}$ alkyl-(optionally substituted aryl). In a preferred embodiment $R^{55}$ is —H or -(optionally substituted $C_{1-6}$ alkyl).

$R^{56}$ is -(optionally substituted hydrocarbon group which contains from 5 to 20 carbon atoms and optionally 1 to 4 heteroatoms selected from O, N and S and which contains at least one ring). Preferably, the at least one ring is aromatic such as an aryl or heteroaryl ring. More preferably, $R^{56}$ is a hydrocarbon group which contains from 5 to 20 carbon atoms and optionally 1 to 4 heteroatoms and which contains at least two rings, wherein the hydrocarbon group can be optionally substituted. Even more preferably, at least one of the at least two rings is aromatic such as an aryl or heteroaryl ring. Preferred examples of $R^{56}$ can be selected from the group consisting of

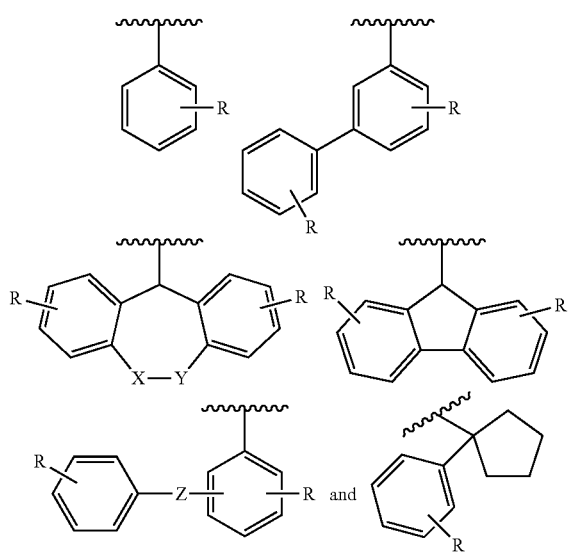

X is absent, $CH_2$, NH, C(O)NH, S or O. Furthermore, Y is $CH_2$.

In an alternative embodiment, X and Y can be joined together to form an annulated, carbo- or heterocyclic 3- to 8-membered ring which can be saturated or unsaturated. Specific examples of X—Y include —$CH_2$—, —$CH_2$—$CH_2$—, —O—, and —NH—.

Z is O or S.

R is independently selected from —H, —$C_{1-6}$ alkyl, —$CF_3$, -halogen, —CN, —OH, and —O—$C_{1-6}$ alkyl.

$R^{57}$ is —H, -Hal or —$C_{1-6}$ alkyl; preferably $R^{57}$ is —H, or —$C_{1-6}$ alkyl.

$R^{58}$ is —H, —$C_{1-6}$ alkyl, or —$(CH_2CH_2O)_rH$; preferably $R^{58}$ is —H, or —$C_{1-6}$ alkyl.

$R^{59}$ is —H, or —$C_{1-6}$ alkyl.

R is independently selected from —$C_{1-6}$ alkyl, —C(O)—$C_{1-6}$ alkyl, -Hal, —$CF_3$, —CN, —COOR$^{58}$, —OR$^{58}$, —$(CH_2)_q$NR$^{58}$R$^{59}$, —C(O)—NR$^{58}$R$^{59}$, and —NR$^{58}$—C(O)—$C_{1-6}$ alkyl. Preferably R is -Hal, —$CF_3$, or —CN; more preferably -Hal, or —$CF_3$.

q is 0 to 4.

r is 1 to 3.

The optional substituent of the alkyl group, aryl group, hydrocarbon group and/or cycloalkyl group is selected from the group consisting of one or more substituents R, which includes —$C_{1-6}$ alkyl, —C(O)—$C_{1-6}$ alkyl, -Hal, —$CF_3$, —CN, —COOR$^{57}$, —OR$^{57}$, —$(CH_2)_q$NR$^{57}$R$^{58}$, —O(O)—NR$^{57}$R$^{58}$, and —NR$^{57}$—C(O)—$C_{1-6}$ alkyl. Preferably, the optional substituent of the aryl group, hydrocarbon group and/or cycloalkyl group is -halogen (preferably F), —$OCH_3$ or —CN. Preferably, the optional substituent of the alkyl group is selected from the group consisting of halogen, —CN, —NR$^{58}$R$^{58}$ (wherein each R$^{58}$ is chosen independently of each other), —OH, and —O—$C_{1-6}$ alkyl. Preferably the substituent of the alkyl group is -halogen, more preferably F.

The present inventors have surprisingly found that the compounds of the present invention which have a bulky moiety $R^{53}$ have improved pharmacological properties compared to corresponding compounds which have a smaller moiety $R^{53}$. Without wishing to be bound by theory it is assumed that the viral polymerase protein has a pocket for binding and that the bulky moiety $R^{53}$ of the compounds of the present invention fills this pocket to a larger extent. It is further assumed that the larger moiety $R^{53}$ is able to provide more hydrophobic interaction with the pocket than smaller moieties such as methyl.

The compounds of the present invention can be administered to a patient in the form of a pharmaceutical composition which can optionally comprise one or more pharmaceutically acceptable excipient(s) and/or carrier(s).

The compounds of the present invention can be administered by various well known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a spray, a tablet, a capsule, a capslet, lozenge, a liposome, a suppository, a plaster, a band-aid, a retard capsule, a powder, or a slow release formulation. Preferably, the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride, may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following non-limiting list:
a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerids and sodium stearyl fumarates,
c) disintegrants such as starches, croscarmellose, sodium methyl cellulose, agar, bentonite, alginic acid, carboxymethyl cellulose, polyvinyl pyrrolidone and the like.

In one embodiment the formulation is for oral administration and the formulation comprises one or more or all of the following ingredients: pregelatinized starch, talc, povidone K 30, croscarmellose sodium, sodium stearyl fumarate, gelatin, titanium dioxide, sorbitol, monosodium citrate, xanthan gum, titanium dioxide, flavoring, sodium benzoate and saccharin sodium.

If a compound of the invention is administered intranasally in a preferred embodiment, it may be administered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoro-alkane such as 1,1,1,2-tetrafluoroethane (HFA 134A™) or 1,1,1,2,3,3,3-heptafluoropropane (HFA 227EA™), carbon dioxide, or another suitable gas. The pressurized container, pump, spray or nebulizer may contain a solution or suspension of the compound of the invention, e.g., using a mixture of ethanol and the propellant as the solvent, which may additionally contain a lubricant, e.g., sorbitan trioleate.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g of the active ingredient (i.e. compound of the invention) per kg body weight. However, in a preferred use of the present invention a compound of the invention is administered to a subject in need thereof in an amount ranging from 1.0 to 500 mg/kg body weight, preferably ranging from 1 to 200 mg/kg body weight. The duration of therapy with a compound of the invention will vary, depending on the severity of the disease being treated and the condition and idiosyncratic response of each individual patient. In one preferred embodiment of a prophylactic or therapeutic use, from 10 mg to 200 mg of the compound are orally administered to an adult per day, depending on the severity of the disease and/or the degree of exposure to disease carriers.

As is known in the art, the pharmaceutically effective amount of a given composition will also depend on the administration route. In general, the required amount will be higher if the administration is through the gastrointestinal tract, e.g., by suppository, rectal, or by an intragastric probe, and lower if the route of administration is parenteral, e.g., intravenous. Typically, a compound of the invention will be administered in ranges of 50 mg to 1 g/kg body weight, preferably 10 mg to 500 mg/kg body weight, if rectal or intragastric administration is used and in ranges of 1 to 100 mg/kg body weight if parenteral administration is used. For intranasal administration, 1 to 100 mg/kg body weight are envisaged.

If a person is known to be at risk of developing a disease treatable with a compound of the invention, prophylactic administration of the biologically active blood serum or the pharmaceutical composition according to the invention may be possible. In these cases the respective compound of the invention is preferably administered in above outlined preferred and particular preferred doses on a daily basis. Preferably, from 0.1 mg to 1 g/kg body weight once a day, preferably 10 to 200 mg/kg body weight. This administration can be continued until the risk of developing the respective viral disorder has lessened. In most instances, however, a compound of the invention will be administered once a disease/disorder has been diagnosed. In these cases it is preferred that a first dose of a compound of the invention is administered one, two, three or four times daily.

The compounds of the present invention are particularly useful for treating, ameliorating, or preventing viral diseases. The type of viral disease is not particularly limited. Examples of possible viral diseases include, but are not limited to, viral diseases which are caused by Poxyiridae, Herpesviridae, Adenoviridae, Papillomaviridae, Polyomaviridae, Parvoviridae, Hepadnaviridae, Retroviridae, Reoviridae, Filoviridae, Paramyxoviridae, Rhabdoviridae, Orthomyxoviridae, Bunyaviridae, Arenaviridae, Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Retroviridae, Filoviridae, Paramyxoviridae, Rhabdoviridae, Orthomyxoviridae, Bunyaviridae, Arenaviridae, Coronaviridae, Picornaviridae, Togaviridae, Flaviviridae, more preferably viral diseases which are caused by orthomyxoviridae.

Examples of the various viruses are given in the following table.

| Family | Virus (preferred examples) |
| --- | --- |
| Poxviridae | Smallpox virus |
| | Molluscum contagiosum virus |
| Herpesviridae | Herpes simplex virus |
| | Varicella zoster virus |
| | Cytomegalovirus |
| | Epstein Barr virus |
| | Kaposi's sarcoma-associated herpesvirus |
| Adenoviridae | Human adenovirus A-F |
| Papillomaviridae | Papillomavirus |
| Polyomaviridae | BK-virus |
| | JC-Virsu |
| Parvoviridae | B19 virus |
| | Adeno associated virus 2/3/5 |
| Hepadnaviridae | Hepatitis B virus |
| Retroviridae | Human immunodeficiency virus types 1/2 |
| | Human T-cell leukemia virus |
| | Human foamy virus |
| Reoviridae | Reovirus 1/2/3 |
| | Rotavirus A/B/C |
| | Colorado tick fever virus |
| Filoviridae | Ebola virus |
| | Marburg virus |
| Paramyxoviridae | Parainfluenza virus 1-4 |
| | Mumps virus |
| | Measles virus |
| | Respiratory syncytial virus |
| | Hendravirus |
| Rhabdoviridae | Vesicular stomatitis virus |
| | Rabies virus |
| | Mokola virus |
| | European bat virus |
| | Duvenhage virus |
| Orthomyxoviridae | Influenza virus types A-C |
| Bunyaviridae | California encephalitis virus |
| | La Crosse virus |
| | Hantaan virus |
| | Puumala virus |
| | Sin Nombre virus |
| | Seoul virus |
| | Crimean- Congo hemorrhagic fever virus |
| | Sakhalin virus |
| | Rift valley virus |
| | Sandfly fever virus |
| | Uukuniemi virus |
| Arenaviridae | Lassa virus |
| | Lymphocytic choriomeningitis virus |
| | Guanarito virus |
| | Junin virus, |
| | Machupo virus |
| | Sabia virus |
| Coronaviridae | Human coronavirus |
| Picornaviridae | Human enterovirus types A-D (Poliovirus, Echovirus, Coxsackie virus A/B) |
| | Rhinovirus types A/B/C |
| | Hepatitis A virus |
| | Parechovirus |
| | Food and mouth disease virus |
| Hepeviridae | Hepatitis E virus |
| Caliciviridae | Norwalk virus |
| | Sapporo virus |
| Astroviridae | Human astrovirus 1 |
| Togaviridae | Ross River virus |
| | Chikungunya virus |
| | O'nyong-nyong virus |
| | Rubella virus |
| Flaviviridae | Tick-borne encephalitis virus |
| | Dengue virus |
| | Yellow Fever virus |
| | Japanese encephalitis virus |
| | Murray Valley virus |
| | St. Louis encephalitis virus |
| | West Nile virus |
| | Hepatitis C virus |
| | Hepatitis G virus |
| | Hepatitis GB virus |

-continued

| Family | Virus (preferred examples) |
| --- | --- |
| Deltavirus | Hepatitis deltavirus |
| Bornaviridae | Bornavirus |
| Prions | |

Preferably, the compounds of the present invention are employed to treat influenza. The present invention covers all virus genera belonging to the family of orthomyxoviridae, specifically influenza virus type A, B, and C, isavirus, and thogotovirus. Within the present invention, the term "influenza" includes influenza caused by any influenza virus such as influenza virus type A, B, and C including their various stains and isolates, and also covers influenza A virus strains commonly referred to as bird flu and swine flu. The subject to be treated is not particularly restricted and can be any vertebrate, such as birds and mammals (including humans).

Without wishing to be bound by theory it is assumed that the compounds of the present invention are capable of inhibiting endonuclease activity, particularly that of influenza virus. More specifically it is assumed that they directly interfere with the N-terminal part of the influenza virus PA protein, which harbors endonuclease activity and is essential for influenza virus replication. Influenza virus replication takes place inside the cell within the nucleus. Thus, compounds designed to inhibit PA endonuclease activity need to cross both the cellular and the nuclear membrane, a property which strongly depends on designed-in physico-chemical properties of the compounds. The present invention shows that the claimed compounds have in vitro endonuclease inhibitory activity and have antiviral activity in vitro in cell-based assays.

A possible measure of the in vitro endonuclease inhibitory activity of the compounds having the formula (V) is the FRET (fluorescence-resonance energy transfer)-based endonuclease activity assay disclosed herein. Preferably, the compounds exhibit a % reduction of at least about 50% at 25 μM in the FRET assay. In this context, the % reduction is the % reduction of the initial reaction velocity (v0) measured as fluorescence increase of a dual-labelled RNA substrate cleaved by the influenza virus endonuclease subunit (PA-Nter) upon compound treatment compared to untreated samples. Preferably, the compounds exhibit an $IC_{50}$ of less than about 40 μM, more preferably less than about 20 μM, in this assay. The half maximal inhibitory concentration ($IC_{50}$) is a measure of the effectiveness of a compound in inhibiting biological or biochemical function and was calculated from the initial reaction velocities (v0) in a given concentration series ranging from maximum 100 μM to at least 2 nM.

The compounds having the general formula (V) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza that has been caused by influenza virus infection and conditions associated with this viral infection such as viral pneumonia or secondary bacterial pneumonia and medicaments to treat symptoms such as chills, fever, sore throat, muscle pains, severe headache, coughing, weakness and fatigue. Furthermore, the compounds having the general formula (I) can be used in combination with anti-inflammatories.

The following combinations of medicaments are envisaged as being particularly suitable:

(i) The combination with endonuclease and cap-binding inhibitors (particularly targeting influenza). The endonuclease inhibitors are not particularly limited and can be any endonuclease inhibitor, particularly any viral endonuclease inhibitor. Preferred endonuclease inhibitors are those as defined in the U.S. applications with the Ser. Nos. 61/550,045 (filed on Oct. 21, 2011), 61/650,713 (filed on May 23, 2012), 61/650,725 (filed on May 23, 2012) and 61/679,968 (filed on Aug. 6, 2012). The complete disclosure of these applications is incorporated herein by reference. In particular, all descriptions with respect to the general formula of the compounds according to these US applications, the preferred embodiments of the various substituents as well as the medical utility and advantages of the compounds are incorporated herein by reference.

Further preferred endonuclease inhibitors are the compounds having the general formula (I) as defined in the copending application Ser. No. 14/149,284, and the compounds having the general formula (II) as defined in the copending application Ser. No. 14/149,218, which were filed on even date herewith, the complete disclosure of which is incorporated by reference. In particular, all descriptions with respect to the general formula of these compounds, the preferred embodiments of the various substituents as well as the medical utility and advantages of the compounds are incorporated herein by reference. These compounds can be optionally in the form of a pharmaceutically acceptable salt, solvate, polymorph, codrug, cocrystal, prodrug, tautomer, racemate, enantiomer, or diastereomer or mixture thereof.

The cap-binding inhibitors are not particularly limited either and can be any cap-binding inhibitor, particularly any viral cap-binding inhibitor. Preferred cap-binding inhibitors are those having the general formula (II) as defined in U.S. application 61/550,057 (filed on Oct. 21, 2011) and/or the compounds disclosed in WO2011/000566, the complete disclosure of which is incorporated by reference. In particular, all descriptions with respect to the general formula of the compounds according to U.S. 61/550,057 or WO2011/000566, the preferred embodiments of the various substituents as well as the medical utility and advantages of the compounds are incorporated herein by reference.

Widespread resistance to both classes of licensed influenza antivirals (M2 ion channel inhibitors (adamantanes) and neuraminidase inhibitors (e.g. oseltamivir)) occurs in both pandemic and seasonal emerging influenza strains, rendering these drugs to be of marginal utility in the treatment modality. For M2 ion channel inhibitors, the frequency of viral resistance has been increasing since 2003 and for seasonal influenza A/H3N2, adamantanes are now regarded as ineffective. Virtually all 2009 H1N1 and seasonal H3N2 strains are resistant to adamantanes (rimantadine and amantadine), and for oseltamivir, the most widely prescribed neuraminidase inhibitor (NAI), the WHO reported on significant emergence of influenza A/H1N1 resistance starting in the influenza season 2007/2008; and for the second and third quarters of 2008 in the southern hemisphere. Even more serious numbers were published for the fourth quarter of 2008 (northern hemisphere) where 95% of all tested isolates revealed no oseltamivir-susceptibility. Considering the fact that now most national governments have been stockpiling NAIs as part of their influenza pandemic preparedness plan, it is obvious that the demand for new, effective drugs is growing significantly. To address the need for more effective therapy, preliminary studies using double or even triple combinations of antiviral drugs with different mechanisms of action have been undertaken. Adamantanes and neuraminidase inhibitors in combination were analysed in vitro and in vivo and were found to act highly synergistically. However, it is known that for both types of antivirals resistant viruses emerge rather rapidly and this issue is not tackled by combining these established antiviral drugs.

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. These two targets are located within distinct subunits of the polymerase complex and thus represent unique drug targets. Due to the fact that both functions are required for the so-called "cap-snatching" mechanism which is essential for viral transcription, concurrent inhibition of both functions is expected to act highly synergistically. This highly efficient drug combination would result in lower substance concentrations and hence improved dose-response-relationships and better side effect profiles.

Both active sites are highly conserved among all influenza A strains (e.g., avian and human) and even influenza B viruses, and hence this high degree of sequence conservation underpins the perception that these targets are not likely to trigger rapid resistant virus generation. Additionally, close interaction with host proteins render these viral proteins less prone to mutations. Thus, endonuclease and cap-binding inhibitors individually and in combination are ideal drug candidates to combat both seasonal and pandemic influenza, irrespectively of the virus strain.

The combination of an endonuclease inhibitor and a cap-binding inhibitor or a dual specific polymerase inhibitor targeting both the endonuclease active site and the cap-binding domain would be effective against virus strains resistant against adamantanes and neuraminidase inhibitors and moreover combine the advantage of low susceptibility to resistance generation with activity against a broad range of virus strains.

(ii) The combination of inhibitors of different antiviral targets (particularly targeting influenza virus) focusing on the combination with (preferably influenza virus) polymerase inhibitors as dual or multiple combination therapy. Influenza virus polymerase inhibitors are novel drugs targeting the transcription and replication activity of the polymerase. Selective inhibitors against the viral polymerase severely attenuate virus infection by stopping the viral reproductive cycle. The combination of a polymerase inhibitor specifically addressing a viral intracellular target with an inhibitor of a different antiviral target is expected to act highly synergistically. This is based on the fact that these different types of antiviral drugs exhibit completely different mechanisms of action requiring different pharmacokinetics properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the first group of polymerase inhibitors (e.g., cap-binding and endonuclease inhibitors) is combined with at least one compound selected from the second group of polymerase inhibitors.

The first group of polymerase inhibitors which can be used in this type of combination therapy includes, but is not limited to, the compounds having the formula (V).

The second group of polymerase inhibitors which can be used in this type of combination therapy includes, but is not limited to, the compounds having the general formula (I) as defined in the U.S. application with the Ser. No. 61/550,045 filed on Oct. 21, 2011, the compounds having the general formula (II) as defined in U.S. application 61/550,057 filed on Oct. 21, 2011, the compounds disclosed in WO 2011/000566, WO 2010/110231, WO 2010/110409, WO 2006/030807 or U.S. Pat. No. 5,475,109 as well as flutimide and analogues, favipiravir and analogues, epigallocatechin gallate and analogues, as well as nucleoside analogs such as ribavirine.

(iii) The combination of polymerase inhibitors with neuraminidase inhibitors

Influenza virus polymerase inhibitors are novel drugs targeting the transcription and replication activity of the polymerase. The combination of a polymerase inhibitor specifically addressing a viral intracellular target with an inhibitor of a different extracellular antiviral target, especially the (e.g., viral) neuraminidase is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the above mentioned first group of polymerase inhibitors is combined with at least one neuraminidase inhibitor.

The neuraminidase inhibitor (particularly influenza neuramidase inhibitor) is not specifically limited. Examples include zanamivir, oseltamivir, peramivir, KDN DANA, FANA, and cyclopentane derivatives.

(iv) The combination of polymerase inhibitors with M2 channel inhibitors

Influenza virus polymerase inhibitors are novel drugs targeting the transcription and replication activity of the polymerase. The combination of a polymerase inhibitor specifically addressing a viral intracellular target with an inhibitor of a different extracellular and cytoplasmic antiviral target, especially the viral M2 ion channel, is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the above mentioned first group of polymerase inhibitors is combined with at least one M2 channel inhibitor.

The M2 channel inhibitor (particularly influenza M2 channel inhibitor) is not specifically limited. Examples include amantadine and rimantadine.

(v) The combination of polymerase inhibitors with alpha glucosidase inhibitors

Influenza virus polymerase inhibitors are novel drugs targeting the transcription and replication activity of the polymerase. The combination of a polymerase inhibitor specifically addressing a viral intracellular target, with an inhibitor of a different host-cell target, especially alpha glucosidase, is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of cellular targets interacting with viral replication with polymerase inhibitors.

Typically, at least one compound selected from the above-mentioned first group of polymerase inhibitors is combined with at least one alpha glucosidase inhibitor.

The alpha glucosidase inhibitor is not specifically limited. Examples include the compounds described in Chang et al., Antiviral Research 2011, 89, 26-34.

(vi) The combination of polymerase inhibitors with ligands of other influenza targets Influenza virus polymerase inhibitors are novel drugs targeting the transcription and replication activity of the polymerase. The combination of a polymerase inhibitor specifically addressing a viral intracellular target with an inhibitor of different extracellular, cytoplasmic or nucleic antiviral targets is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically at least one compound selected from the above mentioned first group of polymerase inhibitors is combined with at least one ligand of another influenza target.

The ligand of another influenza target is not specifically limited. Examples include compounds acting on the sialidase fusion protein (e.g., Fludase (DAS181), siRNAs and phosphorothioate oligonucleotides), signal transduction inhibitors (e.g., ErbB tyrosine kinase, Abl kinase family, MAP kinases, PKCa-mediated activation of ERK signalling) as well as interferon (inducers).

(vii) The combination of (preferably influenza) polymerase inhibitors with a compound used as an adjuvant to minimize the symptoms of the disease (antibiotics, anti-inflammatory agents like COX inhibitors (e.g., COX-1/COX-2 inhibitors, selective COX-2 inhibitors), lipoxygenase inhibitors, EP ligands (particularly EP4 ligands), bradykinin ligands, and/or cannabinoid ligands (e.g., CB2 agonists)). Influenza virus polymerase inhibitors are novel drugs targeting the transcription and replication activity of the polymerase. The combination of a polymerase inhibitor specifically addressing a viral intracellular target with a compound used as an adjuvance to minimize the symptoms of the disease address the causative and symptomatic pathological consequences of viral infection.

This combination is expected to act synergistically because these different types of drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention as indicated by the appended claims in any way.

EXAMPLES

FRET Endonuclease Activity Assay

The influenza A virus (IAV) PA-Nter fragment (amino acids 1-209) harboring the influenza endonuclease activity was generated and purified as described in Dias et al., Nature 2009; Apr. 16; 458(7240), 914-918. The protein was dissolved in buffer containing 20 mM Tris pH 8.0, 100 mM NaCl and 10 mM β-mercaptoethanol and aliquots were stored at −20° C.

A 20 bases dual-labelled RNA oligo with 5'-FAM fluorophore and 3'-BHQ1 quencher was used as a substrate to be cleaved by the endonuclease activity of the PA-Nter. Cleavage of the RNA substrate frees the fluorophore from the quencher resulting in an increase of the fluorescent signal.

All assay components were diluted in assay buffer containing 20 mM Tris-HCl pH 8.0, 100 mM NaCl, 1 mM $MnCl_2$, 10 mM $MgCl_2$ and 10 mM β-mercaptoethanol. The final concentration of PA-Nter was 0.5 μM and 1.6 μM RNA substrate. The test compounds were dissolved in DMSO and generally tested at two concentrations or a concentration series resulting in a final plate well DMSO concentration of 0.5%. In those cases where the compounds were not soluble at that concentration, they were tested at the highest soluble concentration.

5 μl of each compound dilution was provided in the wells of white 384-well microtiter plates (PerkinElmer) in eight replicates. After addition of PA-Nter dilution, the plates were sealed and incubated for 30 min at room temperature prior to the addition of 1.6 μM RNA substrate diluted in assay buffer. Subsequently, the increasing fluorescence signal of cleaved RNA was measured in a microplate reader (Synergy HT, Biotek) at 485 nm excitation and 535 nm emission wavelength. The kinetic read interval was 35 sec at a sensitivity of 35. Fluorescence signal data over a period of 20 min were used to calculate the initial velocity (v0) of substrate cleavage. Final readout was the % reduction of v0 of compound-treated samples compared to untreated. The half maximal inhibitory concentration ($IC_{50}$) is a measure of the effectiveness of a compound in inhibiting biological or biochemical function and was calculated from the initial reaction velocities (v0) in a given concentration series ranging from maximum 100 μM to at least 2 nM.

| Formula no. | FRET |
|---|---|
| 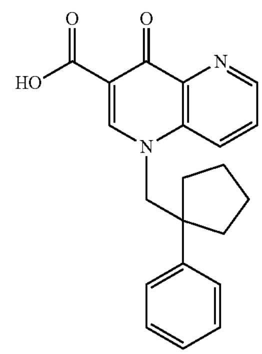 [SMILES: O=C(O)c1cn(CC2(c3ccccc3)CCCC2)c2cccnc2c1=O]  | $IC_{50}$ = 0.6 μM |
| 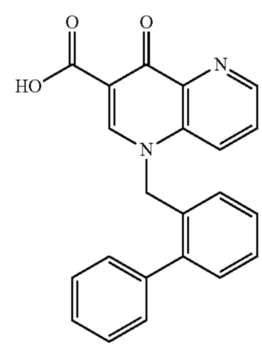 [SMILES: O=C(O)c1cn(Cc2ccccc2-c2ccccc2)c2cccnc2c1=O]  | $IC_{50}$ = 0.76 μM |
| 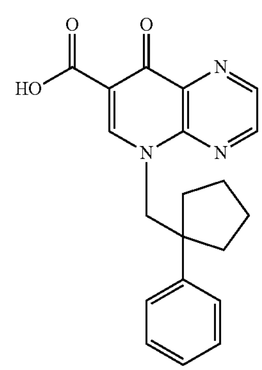 [SMILES: O=C(O)c1cn(CC2(c3ccccc3)CCCC2)c2nccnc2c1=O]  | $IC_{50}$ = 9.7 μM |

-continued

| Formula no. | FRET |
|---|---|
| (structure) | IC$_{50}$ = 7.8 μM |
| (structure) | 6% @ 1 μM |
| (19) | IC$_{50}$ = 1.5 μM |
| (23) | 14% @ 1 μM |

-continued

| Formula no. | FRET |
|---|---|
| (33) | IC$_{50}$ = 0.5 μM |
| (38) | IC$_{50}$ = 6.76 μM |
| (29) | IC$_{50}$ = 0.43 μM |
| (structure) | 7% @ 1 μM |

-continued
| Formula no. | FRET |
|---|---|
| 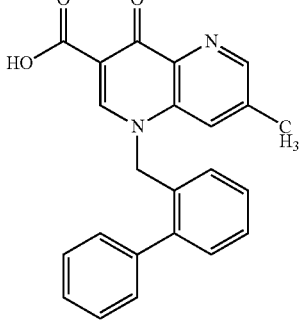 (21) | IC$_{50}$ = 0.57 μM |
| 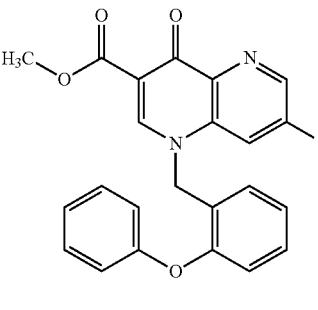 (27) | 33% @ 1 μM |
| 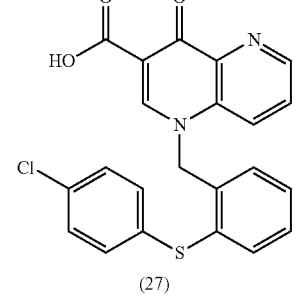 (27) | IC$_{50}$ = 5.6 μM |
Synthetic Route for (7):
Scheme 1
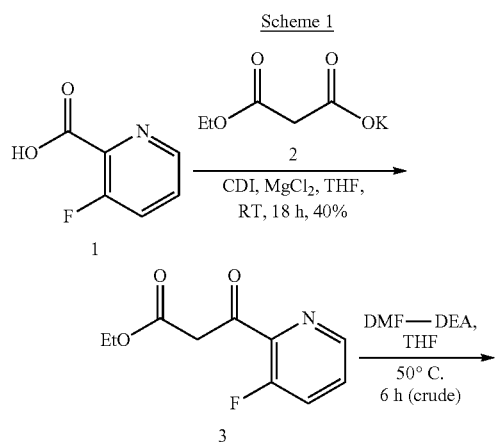
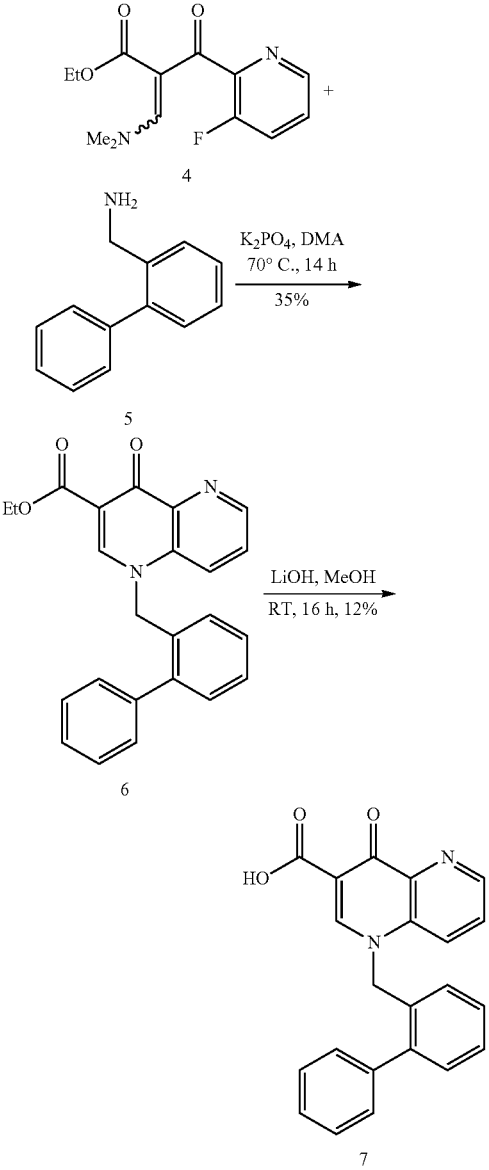
Experimental
Preparation of (3)
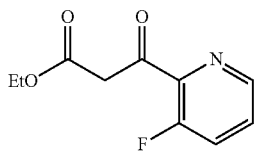 [SMILES: CCOC(=O)CC(=O)c1ncccc1F]
3-(3-Fluoro-pyridin-2-yl)-3-oxo-propionic acid ethyl ester
To a solution of ethyl potassium malonate (2) (452 mg, 2.66 mmol) in tetrahydrofuran (5 mL) was added MgCl$_2$ (202 mg, 2.13 mL). The mixture was stirred at 50° C. for 4 h and then cooled to room temperature. In another flask a solution of 3-fluoro-pyridine-2-carboxylic acid (1) (250 mg, 1.77 mmol) in tetrahydrofuran (5 mL) was taken and CDI (carbonyldiimidazole) (489 mg, 3.01 mmol) was added at 10° C. The mixture was stirred at room temperature for 1 h, this reaction mixture was then added to the above suspension and stirred at room temperature for 18 h. After completion of the reaction, water was added and the mixture was extracted with ethyl acetate. The organic layer was washed with brine, dried over $Na_2SO_4$ and concentrated.

The residue was purified using normal silica gel column chromatography (using 2% methanol:dichloromethane) to get 3-(3-fluoro-pyridin-2-yl)-3-oxo-propionic acid ethyl ester (3) (150 mg, 40%) as a sticky liquid.
LC-MS: 212.4 (M+H).

Preparation of (4)

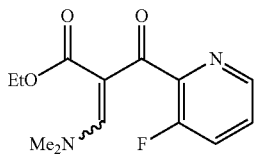

3-Dimethylamino-2-(3-fluoro-pyridine-2-carbonyl)-acrylic acid ethyl ester

To a stirred solution of 3-(3-fluoro-pyridin-2-yl)-3-oxo-propionic acid ethyl ester (3) (15 mg, 0.07 mmol) in 3-hydroxytetrahydrofuran (2 mL) was added slowly dimethylformamide diethylacetale (0.085 mL, 0.5 mmol) at room temperature. The mixture was stirred at 50° C. for 6 h. After completion of the reaction, solvent was evaporated under vacuum to get the crude 3-dimethylamino-2-(3-fluoro-pyridine-2-carbonyl)-acrylic acid ethyl ester (4) (18 mg, crude) as a brown sticky liquid LC-MS: 267.4 (M+H). The crude compound was used in the next step without purification.

Preparation of (6)

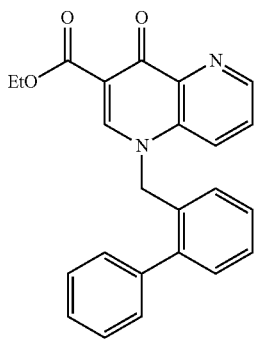

1-Biphenyl-2-ylmethyl-4-oxo-1,4-dihydro-[1,5] naphthyridine-3-carboxylic acid ethyl ester To a stirred solution of 3-dimethylamino-2-(3-fluoro-pyridine-2-carbonyl)acrylic acid ethyl ester (4) (18 mg, 0.067 mmol) in dimethylacetamide (2 mL) was added $K_3PO_4$ (28 mg, 0.14 mmol) followed by C-biphenyl-2-yl-methylamine (5) (11 mg, 0.06 mmol) at room temperature. The mixture was stirred at 70° C. for 14 h. After completion of the reaction, the reaction mixture was poured into ice water and extracted with ethyl acetate. The organic layer was washed with brine, dried over $Na_2SO_4$ and concentrated. The residue was purified using normal silica gel column chromatography (3% methanol:dichloromethane) to get 1-biphenyl-2-ylmethyl-4-oxo-1,4-dihydro-[1,5]naphthyridine-3-carboxylic acid ethyl ester (6) (9 mg, 35%) as a sticky solid.
LC-MS: 385.4 (M+H).

Preparation of (7)

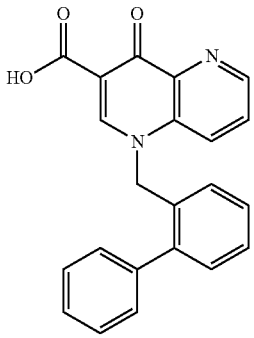

1-Biphenyl-2-ylmethyl-4-oxo-1,4-dihydro-[1,5] naphthyridine-3-carboxylic acid

To a stirred solution of 1-Biphenyl-2-ylmethyl-4-oxo-1,4-dihydro-[1,5]naphthyridine-3-carboxylic acid ethyl ester (6) (850 mg, 2.4 mmol) in MeOH (8 mL) was added LiOH—$H_2O$ (100.2 mg, 4.8 mmol) and stirred at RT for 16 h. After completion of the reaction, distilled-off the solvent from the reaction and diluted with water. The aqueous part was acidified with 2 N HCl, extracted with EtOAC and organic layer was washed with brine. It was dried over $Na_2SO_4$, concentrated and the residue was purified by Prep-HPLC to get 1-Biphenyl-2-ylmethyl-4-oxo-1,4-dihydro-[1,5]naphthyridine-3-carboxylic acid (7) (88 mg, 11%) as off white solid.
LC-MS: 357.4 (M+H).
Synthetic Route for 10:

Scheme 2

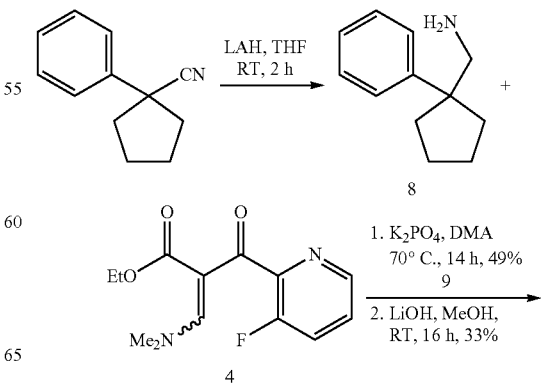

-continued

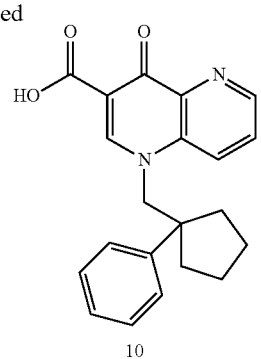

10

Preparation of (8)

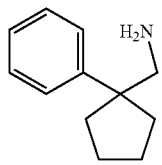 [SMILES: NCC1(c2ccccc2)CCCC1]

C-(1-Phenyl-cyclopentyl)-methylamine

To a stirred solution of 1-phenyl-cyclopentanecarbonitrile (4 g, 23.5 mmol) in tetrahydrofuran (50 mL) was added lithium aluminium hydride slowly (1M in tetrahydrofuran, 70 ml, 70.6 mmol) and the reaction mixture was stirred at room temperature for 2 h. After completion of the reaction, the reaction mixture was quenched with saturated aqueous Na$_2$SO$_4$ solution slowly at 0° C. It was then filtered and the residue was washed with ethyl acetate. The organic part was concentrated to get C-(1-phenyl-cyclopentyl)-methylamine (8) (2.5 g, crude) as a liquid.

LC-MS: 176.2 (M+H).

Preparation of (9)

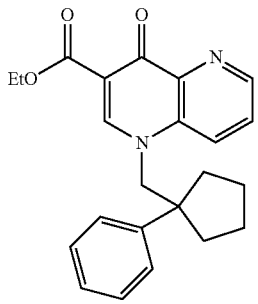 [SMILES: CCOC(=O)c1cn(CC2(c3ccccc3)CCCC2)c2cccnc2c1=O]

4-Oxo-1-(1-phenyl-cyclopentylmethyl)-1,4-dihydro-[1,5]naphthyridine-3-carboxylic acid ethyl ester 4-Oxo-1-(1-phenyl-cyclopentylmethyl)-1,4-dihydro-[1,5]naphthyridine-3-carboxylic acid ethyl ester (9) (140 mg, 49.46%) was synthesized as a sticky liquid from 200 mg of 3-dimethylamino-2-(3-fluoro-pyridine-2-carbonyl)-acrylic acid ethyl ester (4) following the procedure described for 1-biphenyl-2-ylmethyl-4-oxo-1,4-dihydro-[1,5]naphthyridine-3-carboxylic acid ethyl ester (6).

LC-MS: 377.4 (M+H).

Preparation of (10)

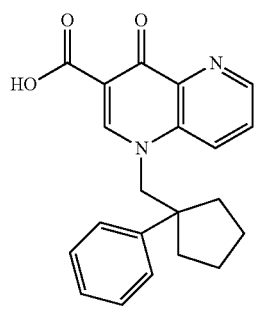 [SMILES: O=C(O)c1cn(CC2(c3ccccc3)CCCC2)c2cccnc2c1=O]

4-Oxo-1-(1-phenyl-cyclopentylmethyl)-1,4-dihydro-[1,5]naphthyridine-3-carboxylic acid 4-Oxo-1-(1-phenyl-cyclopentylmethyl)-1,4-dihydro-[1,5]naphthyridine-3-carboxylic acid (10) (310 mg, 33.46%) was synthesized as an off white solid from 1 g of 4-oxo-1-(1-phenyl-cyclopentylmethyl)-1,4-dihydro-[1,5]naphthyridine-3-carboxylic acid ethyl ester (9) following the procedure described for 1-biphenyl-2-ylmethyl-4-oxo-1,4-dihydro-[1,5]naphthyridine-3-carboxylic acid (7).

LC-MS: 349.4 (M+H).

Synthetic Route for 15:

Scheme 3

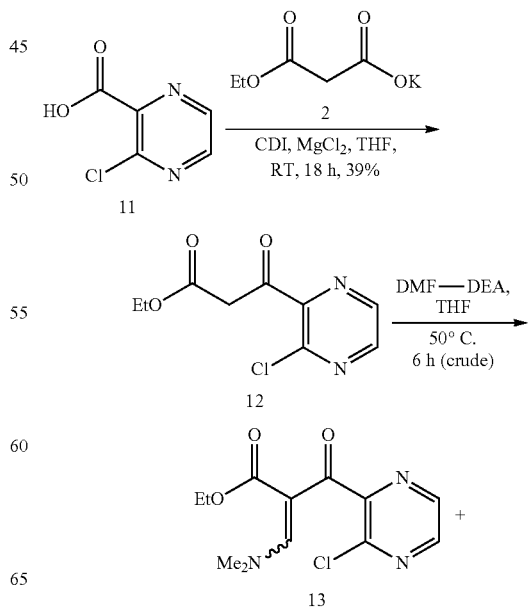

-continued

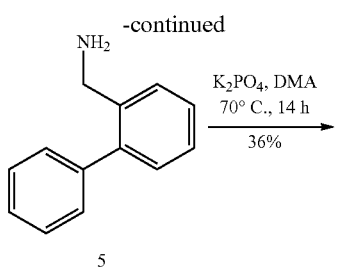

5

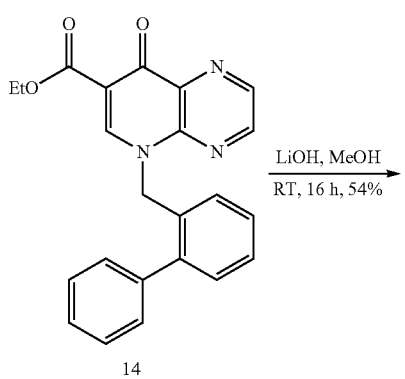

14

Preparation of (12)

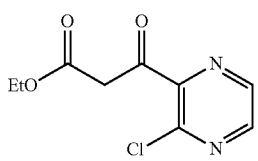 [SMILES: CCOC(=O)CC(=O)c1nccnc1Cl]

3-(3-Chloro-pyrazin-2-yl)-3-oxo-propionic acid ethyl ester 3-(3-Chloro-pyrazin-2-yl)-3-oxo-propionic acid ethyl ester (12) (2 g, 39.54%) was synthesized as a yellow liquid from 3.5 g of 3-chloro-pyrazine-2-carboxylic acid (11) and 5.64 g of ethyl potassium malonate (2) following the procedure described for 3-(3-fluoro-pyridin-2-yl)-3-oxo-propionic acid ethyl ester (3).
LC-MS: 229.2 (M+H).

Preparation of (13)

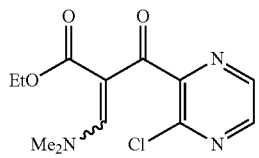 [SMILES: CCOC(=O)C(=CN(C)C)C(=O)c1nccnc1Cl]

2-(3-Chloro-pyrazine-2-carbonyl)-3-dimethylamino-acrylic acid ethyl ester 2-(3-Chloro-pyrazine-2-carbonyl)-3-dimethylamino-acrylic acid ethyl ester (13) (1.2 g, crude) was synthesized as a sticky liquid from 1 g of 3-(3-chloro-pyrazin-2-yl)-3-oxo-propionic acid ethyl ester (12) following the procedure described for 3-dimethylamino-2-(3-fluoro-pyridine-2-carbonyl)-acrylic acid ethyl ester (4).
LC-MS: 284.4 (M+H).

Preparation of (14)

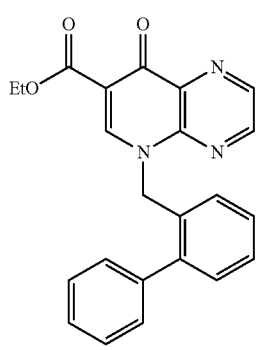 [SMILES: O=C(O)c1cn(Cc2ccccc2-c2ccccc2)c2nccnc2c1=O]

5-Biphenyl-2-ylmethyl-8-oxo-5,8-dihydro-pyrido[2,3-b]pyrazine-7-carboxylic acid ethyl ester 5-Biphenyl-2-ylmethyl-8-oxo-5,8-dihydro-pyrido[2,3-b]pyrazine-7-carboxylic acid ethyl ester (14) (0.600 g, 36.71%) was synthesized as a brown sticky solid from 1.2 g of 2-(3-chloro-pyrazine-2-carbonyl)-3-dimethylamino-acrylic acid ethyl ester (13) following the procedure described for 1-biphenyl-2-ylmethyl-4-oxo-1,4-dihydro-[1,5]naphthyridine-3-carboxylic acid ethyl ester (6).
LC-MS: 386.0 (M+H).

Preparation of (15)

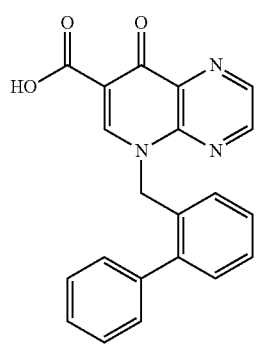

5-Biphenyl-2-ylmethyl-8-oxo-5,8-dihydro-pyrido[2,3-b]pyrazine-7-carboxylic acid 5-Biphenyl-2-ylmethyl-8-oxo-5,8-dihydro-pyrido[2,3-b]pyrazine-7-carboxylic acid (15) (300 mg, 54%) was synthesized as a light yellow solid from 600 mg of 5-biphenyl-2-ylmethyl-8-oxo-5,8-dihydro-pyrido[2,3-b]pyrazine-7-carboxylic acid ethyl ester (14) following the procedure described for 1-biphenyl-2-ylmethyl-4-oxo-1,4-dihydro-[1,5]naphthyridine-3-carboxylic acid (7).

LC-MS: 358.4 (M+H).

Synthetic Route for 17:

8-Oxo-5-(1-phenyl-cyclopentylmethyl)-5,8-dihydro-pyrido[2,3-b]pyrazine-7-carboxylic acid ethyl ester 8-Oxo-5-(1-phenyl-cyclopentylmethyl)-5,8-dihydro-pyrido[2,3-b]pyrazine-7-carboxylic acid ethyl ester (16) (600 mg, 30%) was synthesized as a brown sticky liquid from 1.5 g of 2-(3-chloro-pyrazine-2-carbonyl)-3-dimethylamino-acrylic acid ethyl ester (13) following the procedure described for 1-biphenyl-2-ylmethyl-4-oxo-1,4-dihydro-[1,5]naphthyridine-3-carboxylic acid ethyl ester (6).

LC-MS: 378.4 (M+H).

Preparation of (17)

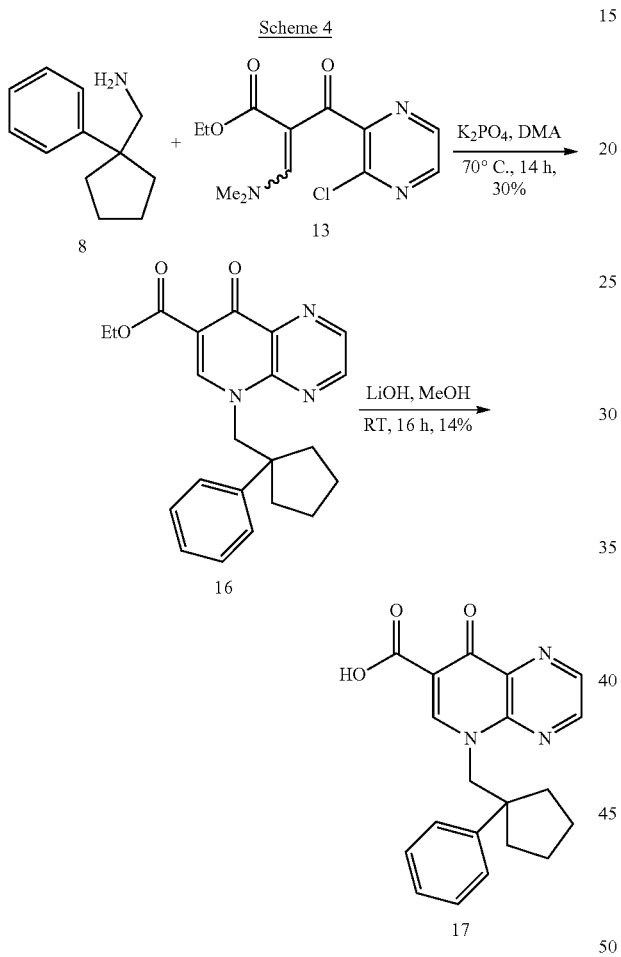

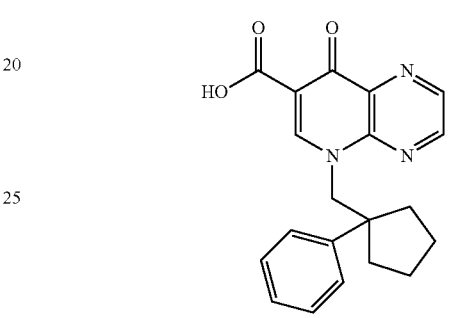

8-Oxo-5-(1-phenyl-cyclopentylmethyl)-5,8-dihydro-pyrido[2,3-b]pyrazine-7-carboxylic acid 8-Oxo-5-(1-phenyl-cyclopentylmethyl)-5,8-dihydro-pyrido[2,3-b]pyrazine-7-carboxylic acid (17) (70 mg, 14%) was synthesized as a yellow solid from 550 mg of 8-oxo-5-(1-phenyl-cyclopentylmethyl)-5,8-dihydro-pyrido[2,3-b]pyrazine-7-carboxylic acid ethyl ester (16) following the procedure described for 1-biphenyl-2-ylmethyl-4-oxo-1,4-dihydro-[1,5]naphthyridine-3-carboxylic acid (7).

LC-MS: 350.4 (M+H).

The following educts (substituted 4-oxo-1,4-dihydro[1,5]napthyridine-3-carboxylic acid derivates) were synthesized according to literature:

Reference 1: *JCS, Perkin Trans* 1: 1980, 1347-1351.

Reference 2: *Bioorg. Med. Chem. Lett;* 2010, 20, 2533-2537.

Preparation of (16)

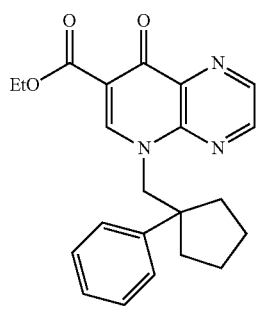 [SMILES: CCOC(=O)c1cn(CC2(c3ccccc3)CCCC2)c2nccnc2c1=O]

Scheme 5

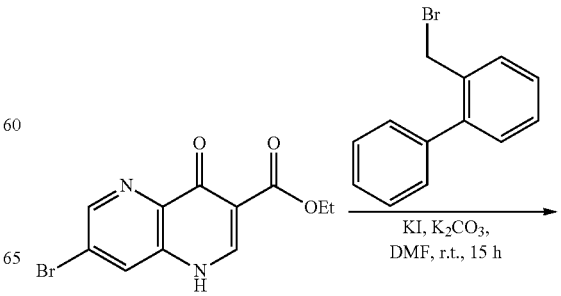

-continued

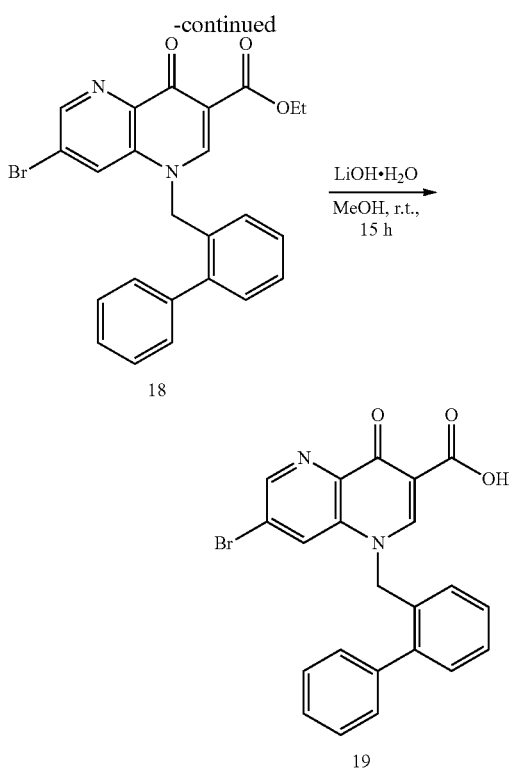

Preparation of (19)

1-(Biphenyl-2-ylmethyl)-7-bromo-4-oxo-1,4-dihydro-1,5-naphthyridine-3-carboxylic acid (19)

Step 1

Ethyl 1-(biphenyl-2-ylmethyl)-7-bromo-4-oxo-1,4-dihydro-1,5-naphthyridine-3-carboxylic acid (18)

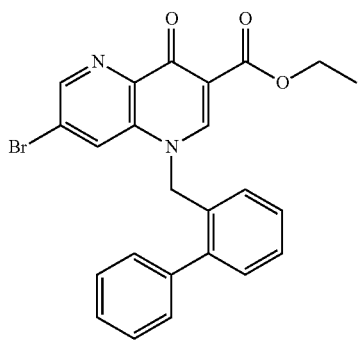 [SMILES: CCOC(=O)c1cn(Cc2ccccc2-c2ccccc2)c2cc(Br)cnc2c1=O]

To a mixture of ethyl 7-bromo-4-oxo-1,4-dihydro-1,5-naphthyridine-3-carboxylate (100 mg, 0.34 mmol), 2-(bromomethyl)biphenyl (91.5 mg, 0.370 mmol), potassium carbonate (140 mg, 1.01 mmol), and potassium iodide (5.59 mg, 0.034 mmol) in a 20 mL vial was added dimethylformamide (10 mL) at room temperature under a nitrogen atmosphere. The nitrogen line was removed from the reaction mixture and the light brown suspension was stirred for 3 days at room temperature at which time LCMS analysis indicated the presence of the desired mass. Then, it was diluted with ~10 mL water and the resulting cloudy solution was poured into approx. 100 mL water. The resulting solids were collected by filtration and washed with water and hexanes. After air drying, 116 mg of ethyl 1-(biphenyl-2-ylmethyl)-7-bromo-4-oxo-1,4-dihydro-1,5-naphthyridine-3-carboxylate (18) (74% yield) was isolated as an off-white solid.

LC/MS calcd. for $C_{24}H_{19}BrN_2O_3$ (m/e) 463.32, obsd. 465.2 [M+H, ES$^+$].

Step 2

1-(Biphenyl-2-ylmethyl)-7-bromo-4-oxo-1,4-dihydro-1,5-naphthyridine-3-carboxylic acid (19)

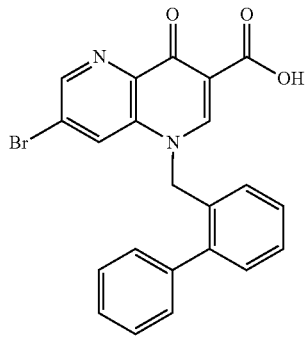 [SMILES: O=C(O)c1cn(Cc2ccccc2-c2ccccc2)c2cc(Br)cnc2c1=O]

To a colorless solution of ethyl 1-(biphenyl-2-ylmethyl)-7-bromo-4-oxo-1,4-dihydro-1,5-naphthyridine-3-carboxylate (18) (50 mg, 0.11 mmol) in methanol (5 mL) was added solid lithium hydroxide monohydrate (22.6 mg, 0.54 mmol) at room temperature. The resulting colorless solution was stirred for 15 h at room temperature at which time LCMS analysis indicated the absence of starting material. Then, the mixture was diluted with water and the methanol was removed under vacuum. The resulting basic aqueous solution was diluted with water (~50 mL) and 1.0N NaOH (~10 mL) and then neutralized with 1.0N HCl. The resulting off-white solids were collected by filtration and washed with water and hexanes. After air drying, 32 mg of 1-(biphenyl-2-ylmethyl)-7-bromo-4-oxo-1,4-dihydro-1,5-naphthyridine-3-carboxylic acid (19) (67% yield) was isolated as an off-white solid.

$^1$H NMR (DMSO-d$_6$) δ: 12.9 (s, 1H), 8.96 (d, J=2.0 Hz, 1H), 8.88 (s, 1H), 8.2 (d, J=2.0 Hz, 1H), 7.26-7.48 (m, 9H), 5.8 (s, 2H).

LC/MS calcd. for $C_{22}H_{15}BrN_2O_3$ (m/e) 435.27, obsd. 437.1 [M+H, ES$^+$].

Preparation of (21)

1-(Biphenyl-2-ylmethyl)-7-methyl-4-oxo-1,4-dihydro-1,5-naphthyridine-3-carboxylic acid (21)

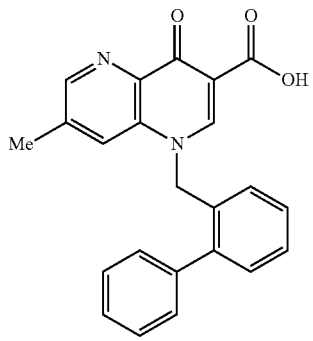 [SMILES: Cc1cnc2c(=O)c(C(=O)O)cn(Cc3ccccc3-c3ccccc3)c2c1]

Step 1

Ethyl 1-(biphenyl-2-ylmethyl)-7-methyl-4-oxo-1,4-dihydro-1,5-naphthyridine-3-carboxyl is acid (20)

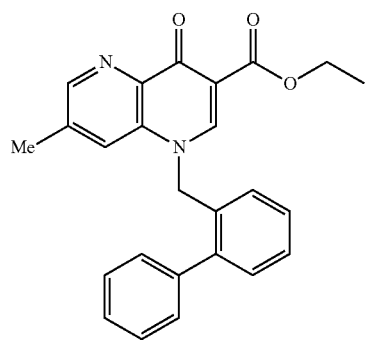 [SMILES: CCOC(=O)c1cn(Cc2ccccc2-c2ccccc2)c2cc(C)cnc2c1=O]

The solid zinc chloride (409 mg, 3.00 mmol) in a 50 mL round bottom flask was melted under high vacuum by heating with a heat gun for 10 minutes. Then, it was cooled to room temperature and dissolved in tetrahydrofuran (5 mL).

In another 2-neck 25 mL round bottom flask was added a 3.0M solution of methylmagnesium bromide (1.00 mL, 3.00 mmol) in tetrahydrofuran to a neat tetrahydrofuran (3 mL) solution. The resulting solution was cooled to −70° C. and then the above prepared zinc chloride solution was added. As a result, a white precipitate was formed which was then allowed to warm to approx. 0° C. in 10 minutes. The resulting white suspension was used directly.

Another 2-neck 50 mL round bottom flask was charged with palladium(II) acetate (67.4 mg, 0.3 mmol) and 2-dicyclohexylphosphino-2',6'-dimethoxybiphenyl (246 mg, 0.6 mmol) at room temperature under a nitrogen atmosphere. Then, it was dissolved in tetrahydrofuran (2 mL). After 5 minutes, a solution of ethyl 1-(biphenyl-2-ylmethyl)-7-bromo-4-oxo-1,4-dihydro-1,5-naphthyridine-3-carboxylate (695 mg, 1.5 mmol) in tetrahydrofuran (5 mL) was added, followed by the above prepared white suspension of methylzincchloride magnesium in tetrahydrofuran. The resulting brown suspension was heated to 55° C. and stirred for 15 h at which time it turned to a black solution and LCMS analysis indicated the absence of starting material. Then, the reaction mixture was quenched with saturated ammonium chloride solution and the organic compound was extracted into ethylacetate (3×70 mL). The combined extracts were washed with water and brine solution, and dried over anhydrous $MgSO_4$. Filtration and concentration gave the crude product (1.2 g) which was purified using an ISCO (80 g) column chromatography, eluting with ethyl acetate in hexanes (0 to 100%) and then 10% methanol and dichloromethane. The desired fractions were combined and the solvent was removed under vacuum to obtain ethyl 1-(biphenyl-2-ylmethyl)-7-methyl-4-oxo-1,4-dihydro-1,5-naphthyridine-3-carboxylate (20) (80 mg, 13.4% yield) as a yellow solid.

LC/MS calcd. for $C_{25}H_{23}N_2O_3$ (m/e) 398.4, obsd. 399.2 [M+H, ES$^+$].

Step 2

1-(Biphenyl-2-ylmethyl)-7-methyl-4-oxo-1,4-dihydro-1,5-naphthyridine-3-carboxylic acid (21)

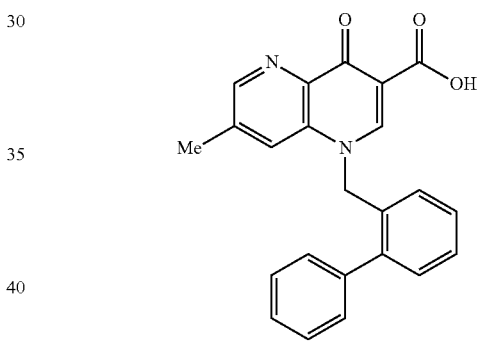

To a solution of ethyl 1-(biphenyl-2-ylmethyl)-7-methyl-4-oxo-1,4-dihydro-1,5-naphthyridine-3-carboxylate (20) (80 mg, 0.2 mmol) in methanol (10 mL) was added the solid lithium hydroxide monohydrate (168 mg, 4.02 mmol) at room temperature under nitrogen atmosphere. It gave a clear solution within 30 minutes and this light yellow solution was stirred for 15 h at which time LCMS analysis indicated the absence of starting material. Then, it was diluted with water and the methanol was removed under vacuum. The basic aqueous layer was diluted with water and then extracted with ethyl acetate (50 mL) to remove any neutral impurities. Then, the basic aqueous layer was neutralized with 1.0N HCl. Then, the acid was extracted with ethyl acetate (2×30 mL) and the combined extracts were washed with brine solution and dried over anhydrous $MgSO_4$. Filtration and concentration gave the yellow solids which were dissolved in acetonitrile and water. The mixture was frozen and then lyophilized under high vacuum to obtain 1-(biphenyl-2-ylmethyl)-7-methyl-4-oxo-1,4-dihydro-1,5-naphthyridine-3-carboxylic acid (21) (15 mg, 20% yield) as a light yellow solid.

$^1$H NMR (DMSO-d$_6$) δ: 12.9 (s, 1H), 8.93 (s, 1H), 8.75 (d, J=2.0 Hz, 1H), 864 (d, J=2 Hz, 1H), 7.19-7.48 (m, 9H), 5.78

(s, 2H), 2.4 (s, 3H). LC/MS calcd. for $C_{23}H_{18}N_2O_3$ (m/e) 370.4, obsd. 371.2 [M+H, ES$^+$].

Preparation of (23)

7-Bromo-4-oxo-1-(2-phenoxybenzyl)-1,4-dihydro-1,5-naphthyridine-3-carboxylic acid (23)

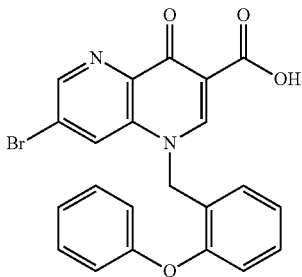

Step 1

Ethyl 7-bromo-4-oxo-1-(2-phenoxybenzyl)-1,4-dihydro-1,5-naphthyridine-3-carboxylic acid (22)

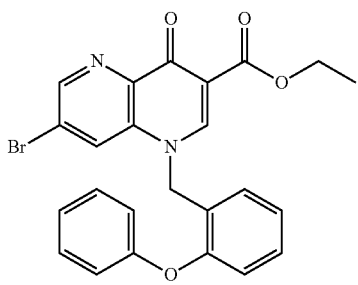 [SMILES: CCOC(=O)c1cn(Cc2ccccc2Oc2ccccc2)c2cc(Br)cnc2c1=O]

To a mixture of ethyl 7-bromo-4-oxo-1,4-dihydro-1,5-naphthyridine-3-carboxylate (150 mg, 0.51 mmol), 1-(chloromethyl)-2-phenoxybenzene (121 mg, 0.56 mmol), potassium carbonate (209 mg, 1.51 mmol), and potassium iodide (92.2 mg, 0.56 mmol) in a 20 mL vial was added dimethylformamide (10 mL) at room temperature under a nitrogen atmosphere. The nitrogen line was removed from the reaction mixture and the light brown suspension was stirred for 2 days at room temperature at which time LCMS analysis indicated the presence of the desired mass. Then, approx. 10 mL of water was added and the resulting cloudy solution was poured into approx. 100 mL water with shaking with a spatula. The resulting white solids were extracted into ethyl acetate (2×50 mL) and the combined extracts were washed with brine solution and dried over anhydrous MgSO$_4$. Filtration and concentration gave ethyl 7-bromo-4-oxo-1-(2-phenoxybenzyl)-1,4-dihydro-1,5-naphthyridine-3-carboxylate (22) (232 mg, 96% yield) as a brown oil.

LC/MS calcd. for $C_{24}H_{19}BrN_2O_4$ (m/e) 479.32, obsd. 481.1 [M+H, ES$^+$].

Step 2

7-Bromo-4-oxo-1-(2-phenoxybenzyl)-1,4-dihydro-1,5-naphthyridine-3-carboxylic acid (23)

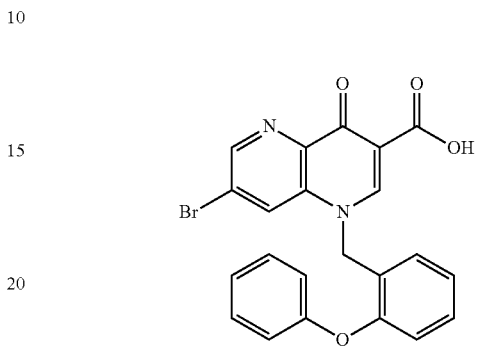

To a light brown solution of ethyl 7-bromo-4-oxo-1-(2-phenoxybenzyl)-1,4-dihydro-1,5-naphthyridine-3-carboxylate (22) (230 mg, 0.5 mmol) in methanol (20 mL) was added the solid lithium hydroxide monohydrate (438 mg, 10.4 mmol) at room temperature. The resulting light brown solution was stirred for 15 h at room temperature at which time LCMS analysis indicated the absence of starting material. Then, it was diluted with water and the methanol was removed under vacuum. The resulting brown paste was difficult to dissolve in 1.0N NaOH and water. Then, the neutral impurities were extracted into ethyl acetate and the basic aqueous layer was diluted with water (~100 mL). Then, the basic aqueous solution was neutralized with 1.0N HCl. The resulting solids were collected by filtration and washed with water and hexanes. After air drying, 40 mg of 7-bromo-4-oxo-1-(2-phenoxybenzyl)-1,4-dihydro-1,5-naphthyridine-3-carboxylic acid (23) (17% yield) was isolated as an off-white solid.

$^1$H NMR (DMSO-d$_6$) δ: 12.9 (s, 1H), 9.27 (s, 1H), 9.05 (s, 1H), 8.7 (s, 1H), 7.36-7.47 (m, 3H), 6.96-7.2 (m, 6H), 5.9 (s, 2H).

LC/MS calcd. for $C_{22}H_{15}BrN_2O_4$ (m/e) 451.27, obsd. 453.1 [M+H, ES$^+$].

Scheme 6

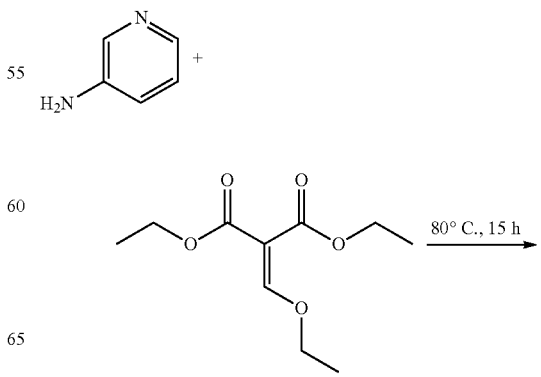

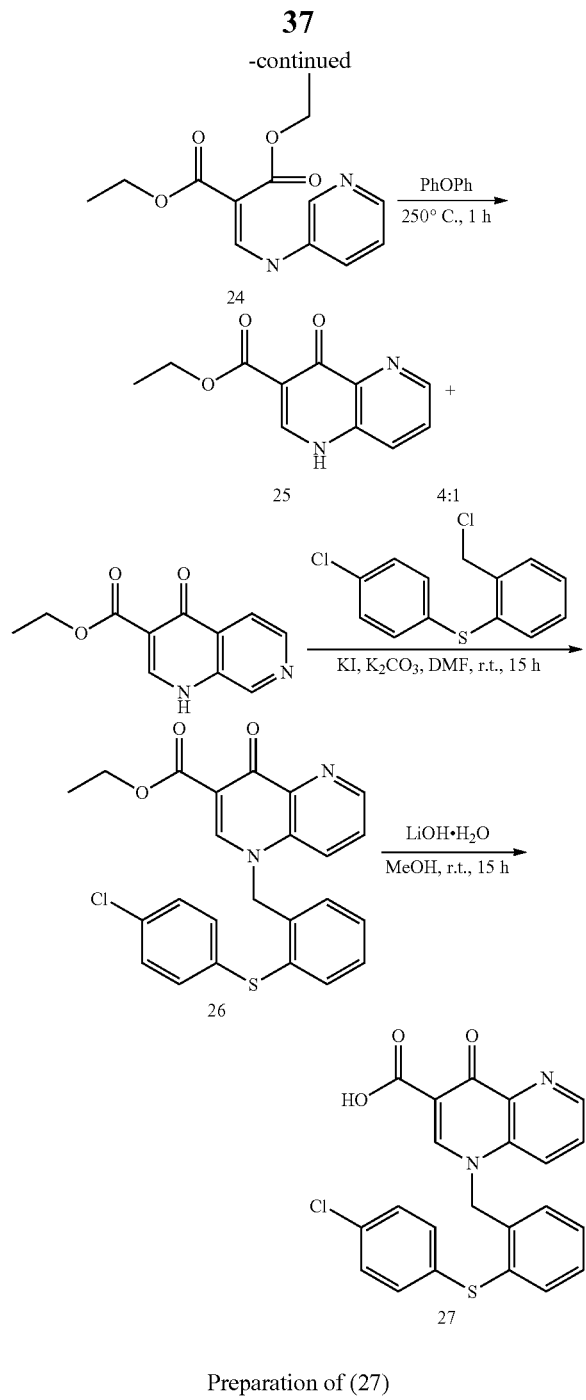

Preparation of (27)

1-(2-(4-Chlorophenylthio)benzyl)-4-oxo-1,4-dihydro-1,5-naphthyridine-3-carboxylic acid (27)

Step 1

Diethyl 2-((pyridine-3-ylamino)methylene)malonate (24)

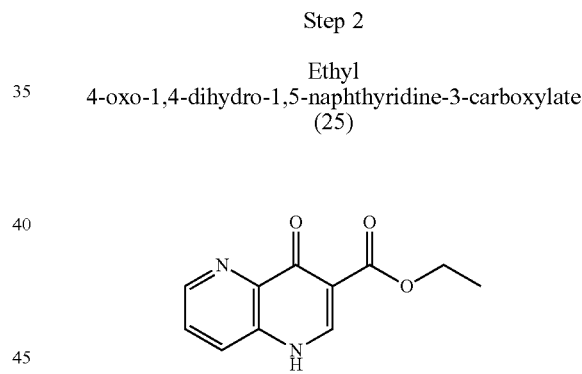

Pyridin-3-amine (9.41 g, 100 mmol) and diethyl 2-(ethoxymethylene)malonate (21.6 g, 100 mmol) were combined in a 250 mL screw capped vessel and this mixture was placed into a preheated oil bath at 80° C. and the resulting light brown solution was stirred for 15 h at which time LCMS analysis indicated the presence of a new spot. Then, the light brown solution was cooled to room temperature and as a result some solids started to form. The mixture was left at room temperature for 2 h. The solids were hard to break, but the big chunks were collected by filtration and washed with hexanes. After air drying, 25.18 g of diethyl 2-((pyridin-3-ylamino)methylene)malonate (24) (95.3% yield) was isolated as a white solid.

LC/MS calcd. for $C_{13}H_{16}N_2O_4$ (m/e) 264.28, obsd. 265.2 [M+H, ES$^+$].

Step 2

Ethyl 4-oxo-1,4-dihydro-1,5-naphthyridine-3-carboxylate (25)

To a hot (248° C., mantle and thermometer were used) and colorless solution of diphenyl ether (100 mL) was added dropwise a light brown solution of diethyl 2-((pyridin-3-ylamino)methylene)malonate (24) (3 g, 11.4 mmol) in diphenyl ether (4 mL, heated to dissolve) at 248° C. for 10 min. During the addition, the reaction mixture turned to a brown solution and then to a dark brown solution. The resulting brown reaction mixture was refluxed (inside temperature was 245 to 248° C.) for 1 h. Then, the heating was stopped and it was allowed to cool to approx. 80° C. at which time some solids started to precipitate and then the mantle was removed. The resulting suspension was poured into approx. 300 mL of hexanes and the brown solids were collected by filtration and washed with hexanes. $^1$H NMR and LCMS analysis of this solid indicated the presence of two regioisomers in a ratio of approx. 4:1. Then, the two peaks were separated by HPLC method and the desired ethyl 4-oxo-1,4-dihydro-1,5-naphthyridine-3-carboxylate (25) (1.25 g, 50% yield) was isolated as a brown solid.

LC/MS calcd. for $C_{11}H_{10}N_2O_3$ (m/e) 218.21, obsd. 219.2 [M+H, ES$^+$].

Step 3

Ethyl 1-(2-(4-chlorophenylthio)benzyl)-4-oxo-1,4-dihydro-1,5-naphthyridine-3-carboxylic acid (26)

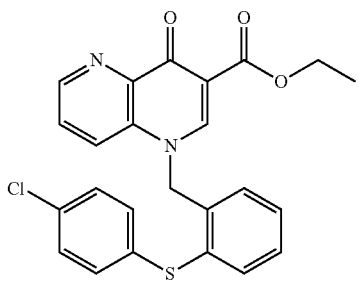 [SMILES: CCOC(=O)c1cn(Cc2ccccc2Sc2ccc(Cl)cc2)c2cccnc2c1=O]

To a mixture of ethyl 4-oxo-1,4-dihydro-1,5-naphthyridine-3-carboxylate (218 mg, 1.0 mmol), (2-(chloromethyl)phenyl)(4-chlorophenyl)sulfane (25) (296 mg, 1.1 mmol), potassium carbonate (415 mg, 3.00 mmol), and potassium iodide (183 mg, 1.1 mmol) in a 20 mL vial was added dimethylformamide (15 mL) at room temperature under a nitrogen atmosphere. The nitrogen line was removed from the reaction mixture and the light brown suspension was stirred for 15 h at room temperature at which time LCMS analysis indicated the presence of the desired mass. Then, approx. 10 mL of water was added and the organic compound was extracted into ethyl acetate (2×100 mL). The combined extracts were washed with brine solution and dried over anhydrous MgSO$_4$. Filtration and concentration gave the crude brown paste which was purified using ISCO (80 g) column chromatography, eluting with ethyl acetate in hexanes (0 to 100%) and then with 5% methanol in dichloromethane to obtain ethyl 1-(2-(4-chlorophenylthio)benzyl)-4-oxo-1,4-dihydro-1,5-naphthyridine-3-carboxylate (26) (208 mg, 46% yield) as a light brown oil.

LC/MS calcd. for C$_{24}$H$_{19}$ClN$_2$O$_3$S (m/e) 450.94, obsd. 451.2 [M+H, ES$^+$].

Step 4

1-(2-(4-Chlorophenylthio)benzyl)-4-oxo-1,4-dihydro-1,5-naphthyridine-3-carboxylic acid (27)

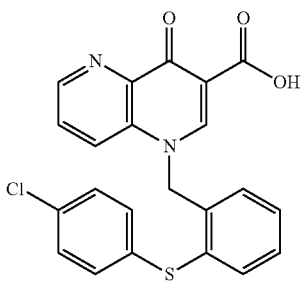 [SMILES: O=C(O)c1cn(Cc2ccccc2Sc2ccc(Cl)cc2)c2cccnc2c1=O]

To a light brown solution of ethyl 1-(2-(4-chlorophenylthio)benzyl)-4-oxo-1,4-dihydro-1,5-naphthyridine-3-carboxylate (26) (203 mg, 0.450 mmol) in methanol (20 mL) was added the solid lithium hydroxide monohydrate (189 mg, 4.5 mmol) at room temperature. The resulting light brown solution was stirred for 15 h at room temperature at which time LCMS analysis indicated the absence of starting material. Then, it was diluted with water and the methanol was removed under vacuum. The resulting light brown solids were difficult to dissolve in 1.0N NaOH and water, but it was dissolved in dimethylformamide (approx. 10 mL) and the solution was diluted with water (approx. 100 mL). Then, the resulting basic aqueous solution was neutralized with 1.0N HCl. The resulting solids were collected by filtration and washed with water and hexanes. After air drying, 102 mg of 1-(2-(4-chlorophenylthio)benzyl)-4-oxo-1,4-dihydro-1,5-naphthyridine-3-carboxylic acid (27) (53.6% yield) was isolated as an off-white solid.

$^1$H NMR (DMSO-d$_6$) δ: 12.8 (br. s., 1H), 9.18 (s, 1H), 8.9 (d, J=6.0 Hz, 1H), 8.05 (d, J=8 Hz, 1H), 7.84 (dd, J=5.9, 2.2 Hz, 1H), 7.52 (d, J=6.5 Hz, 1H), 7.34-7.44 (m, 4H), 7.1-7.17 (m, 3H), 5.9 (s, 2H).

LC/MS calcd. for C$_{22}$H$_{15}$ClN$_2$O$_3$S (m/e) 422.88, obsd. 423.2 [M+H, ES$^+$].

Preparation of (29)

1-((4'-Chlorobiphenyl-2-yl)methyl)-4-oxo-1,4-dihydro-1,5-naphthyridine-3-carboxylic acid (29)

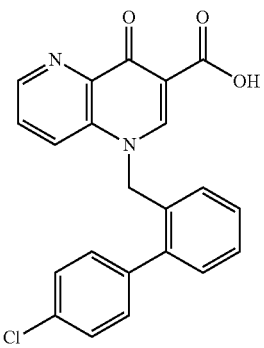 [SMILES: O=C(O)c1cn(Cc2ccccc2-c2ccc(Cl)cc2)c2cccnc2c1=O]

Step 1

Ethyl 1-((4'-chlorobiphenyl-2-yl)methyl)-4-oxo-1,4-dihydro-1,5-naphthyridine-3-carboxylic acid (28)

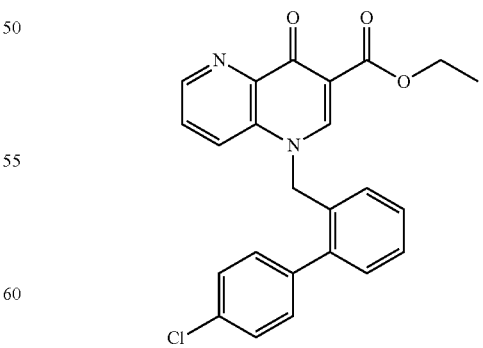

To a mixture of ethyl 4-oxo-1,4-dihydro-1,5-naphthyridine-3-carboxylate (25) (235 mg, 1.08 mmol), 4'-chloro-2-(chloromethyl)biphenyl (281 mg, 1.18 mmol), potassium carbonate (447 mg, 3.23 mmol), and potassium iodide (197 mg, 1.18 mmol) in a 20 mL vial was added dimethylformamide (12 mL) at room temperature under a nitrogen atmosphere. The nitrogen line was removed from the reaction mixture and the light brown suspension was stirred for 3 days at room temperature at which time LCMS analysis indicated the presence of desired mass. Then, approx. 10 mL of water was added and it became a cloudy solution which was then poured into approx. 100 mL of water with shaking with spatula. As a result, a lot of off-white solids were formed, but they were not good solids. Then, the organic compound was extracted into ethyl acetate (2×100 mL) and the combined extracts were washed with brine solution and dried over anhydrous MgSO$_4$. Filtration and concentration gave the crude light brown solid which was purified using ISCO (80 g) column chromatography, eluting with ethyl acetate in hexanes (0 to 100%) and then with 5-10% methanol in dichloromethane to obtain the desired ethyl 1-((4'-chlorobiphenyl-2-yl)methyl)-4-oxo-1,4-dihydro-1,5-naphthyridine-3-carboxylate (28) (257 mg, 57% yield) as a light brown solid.

LC/MS calcd. for $C_{24}H_{19}ClN_2O_3$ (m/e) 418.87, obsd. 421.0 [M+H, ES$^+$].

Step 2

1-((4'-Chlorobiphenyl-2-yl)methyl)-4-oxo-1,4-dihydro-1,5-naphthyridine-3-carboxylic acid (29)

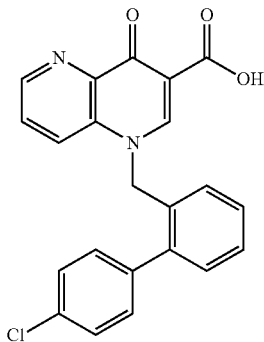 [SMILES: O=C(O)c1cn(Cc2ccccc2-c2ccc(Cl)cc2)c2cccnc2c1=O]

To a brown solution of ethyl 1-((4'-chlorobiphenyl-2-yl)methyl)-4-oxo-1,4-dihydro-1,5-naphthyridine-3-carboxylate (28) (257 mg, 0.61 mmol) in methanol (15 mL) was added the solid lithium hydroxide monohydrate (515 mg, 12.3 mmol) at room temperature under a nitrogen atmosphere. It gave a clear solution within 30 minutes and the resulting dark brown solution was stirred for 15 h at which time LCMS analysis indicated the absence of starting material. Then, the mixture was diluted with water and the methanol was removed under vacuum. The basic aqueous layer was diluted with water and the brown solids were filtered off using filter paper. Then, the filtrate was neutralized with 1.0N HCl. The precipitated off-white solids were collected by filtration and washed with water and hexanes. After drying in air, 165 mg of 1-((4'-chlorobiphenyl-2-yl)methyl)-4-oxo-1,4-dihydro-1,5-naphthyridine-3-carboxylic acid (29) (68.8% yield) was isolated as an off-white solid.

$^1$H NMR (DMSO-d$_6$) δ: 12.8 (br. s., 1H), 9.0 (s, 1H), 8.9 (d, J=4.0 Hz, 1H), 7.9 (d, J=8 Hz, 1H), 7.75-7.8 (m, 1H), 7.25-7.5 (m, 7H), 7.05 (d, J=8 Hz, 1H), 5.8 (s, 2H).

LC/MS calcd. for $C_{22}H_{15}ClN_2O_3$ (m/e) 422.88, obsd. 423.2 [M+H, ES$^+$].

Preparation of (33)

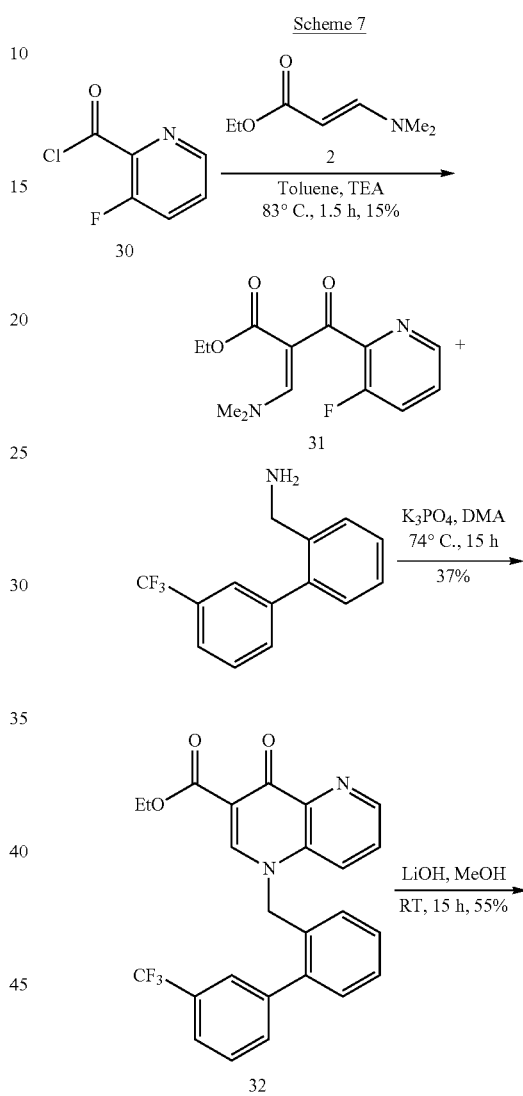

1-oxo-1-((3'-(trifluoromethyl)biphenyl-2-yl)methyl)-
1,4-dihydro-1,5-naphthyridine-3-carboxylic acid
(33)

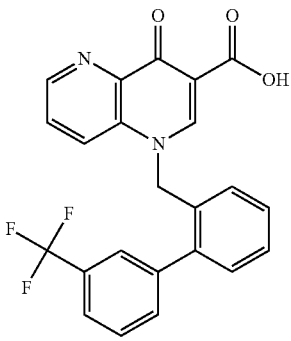 [SMILES: O=C(O)c1cn(Cc2ccccc2-c2cccc(C(F)(F)F)c2)c2cccnc2c1=O]

Step 1

3-Fluoropicolinoyl chloride (30)

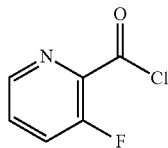

A suspension of 3-fluoropicolinic acid (4.23 g, 30 mmol) and thionyl chloride (35.7 g, 21.9 ml, 300 mmol) was heated to reflux for 15 h at which time it became a dark brown solution. Then, the heating was stopped and the reaction mixture was allowed to cool to room temperature and it was diluted with toluene. Then, the solvent and excess thionyl chloride were removed under vacuum. The residue was azeotrophed one more time with toluene and the resulting brown residue was dried under high vacuum to obtain 3-fluoropicolinoyl chloride (30) (4.70 g, 98.2% yield) as a brown paste which was used directly in the next step.

Step 2

(Z)-Ethyl 3-(dimethylamino)-2-(3-fluoropicolinoyl) acrylate (31)

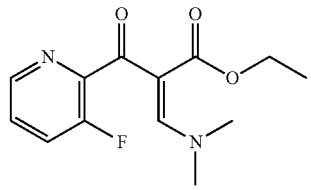 [SMILES: CCOC(=O)/C(=C\N(C)C)C(=O)c1ncccc1F]

To a light yellow solution of (E)-ethyl 3-(dimethylamino) acrylate (5.15 g, 36.0 mmol) in toluene (50 mL) was added triethylamine (3.64 g, 5.02 mL, 36.0 mmol) at room temperature. To this, a dark brown suspension of 3-fluoropicolinoyl chloride (30) (4.79 g, 30 mmol) in toluene (50 mL, heated to dissolve, but not dissolved completely) was added in one portion using a funnel. Then, the resulting dark brown solution was heated to 83° C. and stirred for 1.5 h at this temperature. During this period, it turned to a dark brown solution and TLC analysis indicated the presence of a new spot. Then, the heating was stopped and the dark brown mixture was diluted with ethyl acetate (200 mL) and the brown solution was washed with water, brine solution, and dried over anhydrous MgSO$_4$. Filtration and concentration gave the crude brown mixture which was purified using ISCO (120 g) column chromatography, eluting with ethyl acetate in hexanes (0 to 100%) and then 5 to 20% methanol in dichloromethane. The desired fractions were combined and the solvent was removed under vacuum to obtain the (Z)-ethyl 3-(dimethylamino)-2-(3-fluoropicolinoyl)acrylate (31) (1.33 g, 15% yield) as a dark brown paste.

LC/MS calcd. for C$_{13}$H$_{15}$FN$_2$O$_3$ (m/e) 266.27, obsd. 267.2 [M+H, ES$^+$].

Step 3

Ethyl 1-oxo-1-((3'-(trifluoromethyl)biphenyl-2-yl) methyl)-1,4-di hydro-1,5-naphthyridine-3-carboxylic acid (32)

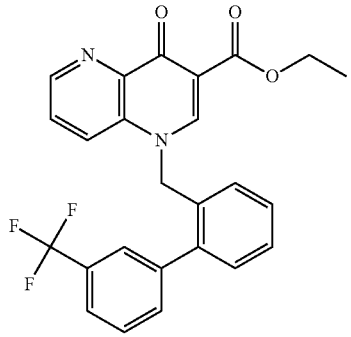 [SMILES: CCOC(=O)c1cn(Cc2ccccc2-c2cccc(C(F)(F)F)c2)c2cccnc2c1=O]

To a brown solution of (Z)-ethyl 3-(dimethylamino)-2-(3-fluoropicolinoyl)acrylate (31) (200 mg, 0.751 mmol) in DMA (dimethylacetamide) (8 mL) in a 20 mL vial were added a solid powder of tribasic potassium phosphate (399 mg, 1.88 mmol) and (3'-(trifluoromethyl)biphenyl-2-yl) methanamine (208 mg, 0.826 mmol) at room temperature under a nitrogen atmosphere. The resulting brown suspension was heated to 74° C. and stirred for 15 h at which time LCMS analysis indicated the absence of starting material. Then, it was cooled to room temperature and poured slowly into water (100 mL), but no solids precipitated. Then, the organic compound was extracted with dichloromethane and the combined extracts were washed with water and brine solution, and dried over anhydrous MgSO$_4$. Filtration and concentration gave the crude brown oil which was purified using ISCO (120 g) column chromatography, eluting with ethyl acetate in hexanes (0 to 100%) and then 5 to 10% methanol in dichloromethane. The desired fractions were combined and the solvent was removed under vacuum to obtain ethyl 4-oxo-1-((3'-(trifluoromethyl)biphenyl-2-yl)methyl)-1,4-dihydro-1,5-naphthyridine-3-carboxylate (32) (126 mg, 37% yield) as a light brown solid.

Step 4

1-Oxo-1-((3'-(trifluoromethyl)biphenyl-2-yl)methyl)-1,4-dihydro-1,5-naphthyridine-3-carboxylic acid (33)

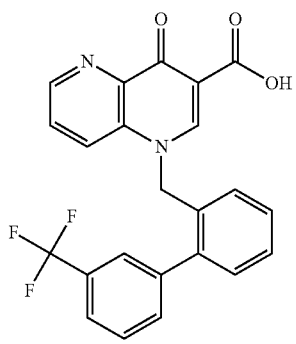 [SMILES: O=C(O)c1cn(Cc2ccccc2-c2cccc(C(F)(F)F)c2)c2cccnc2c1=O]

To a light brown solution of ethyl 4-oxo-1-((3'-(trifluoromethyl)biphenyl-2-yl)methyl)-1,4-dihydro-1,5-naphthyridine-3-carboxylate (32) (114 mg, 0.252 mmol) in methanol (10 mL) was added the solid lithium hydroxide monohydrate (211 mg, 5.04 mmol) at room temperature under a nitrogen atmosphere. The resulting brown solution was stirred for 15 h at which time LCMS analysis indicated the absence of starting material. Then, the reaction mixture was diluted with water and the methanol was removed under vacuum. The basic aqueous solution contains some solids which were dissolved by addition of 5 mL of dimethylformamide and then it was neutralized with 1.0N HCl. Then, the organic compound was extracted into ethyl acetate (2×50 mL) and the combined extracts were washed with brine solution and dried over anhydrous MgSO$_4$. Filtration and concentration gave the crude oil (may contain some dimethylformamide) which was diluted with acetonitrile and water. Then, it was frozen and lyophilized over 3 days to isolate 4-oxo-1-((3'-(trifluoromethyl)biphenyl-2-yl)methyl)-1,4-dihydro-1,5-naphthyridine-3-carboxylic acid (33) (59 mg, 55% yield) as a light brown solid.

$^1$H NMR (DMSO-d$_6$) δ: 12.8 (br. s., 1H), 8.96 (s, 1H), 8.89 (d, J=6.0 Hz, 1H), 8.0 (d, J=8 Hz, 1H), 7.63-7.8 (m, 5H), 7.3-7.48 (m, 3H), 7.08 (d, J=8 Hz, 1H), 5.84 (s, 2H).

LC/MS calcd. for C$_{23}$H$_{15}$F$_3$N$_2$O$_3$ (m/e) 424.37, obsd. 425.2 [M+H, ES$^+$].

Preparation of (38)

Scheme 8

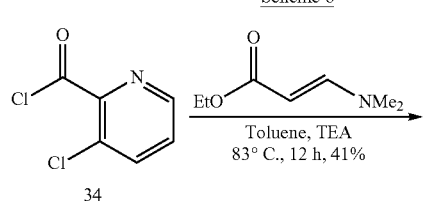

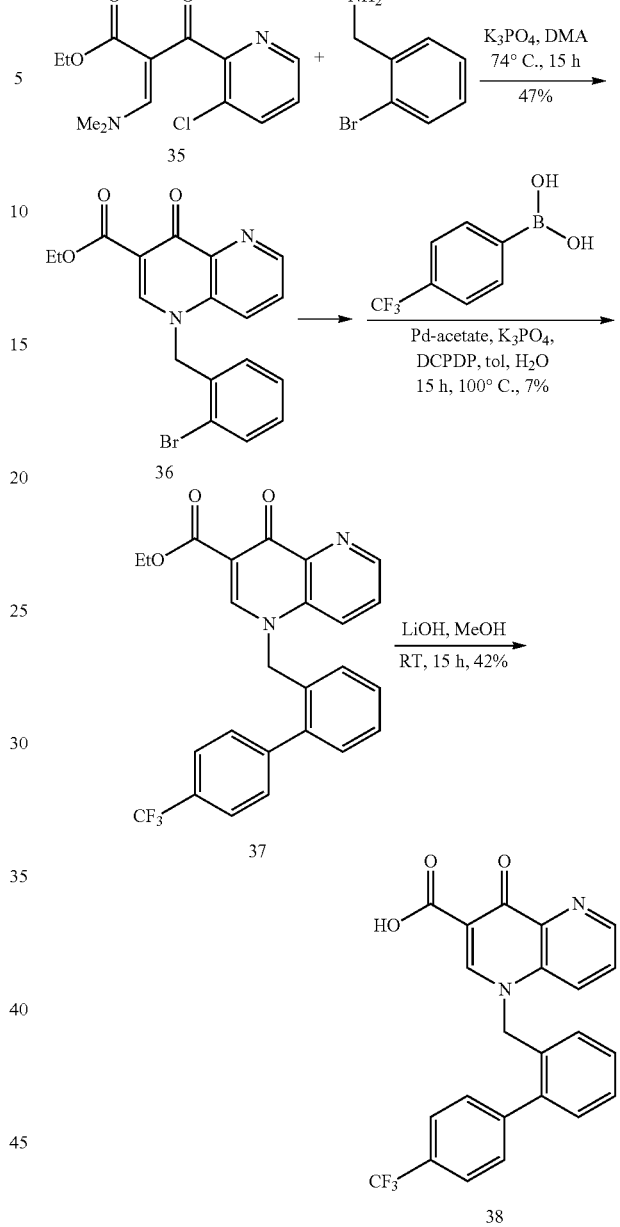

1-Oxo-1-((4'-(trifluoromethyl)biphenyl-2-yl)methyl)-1,4-dihydro-1,5-naphthyridine-3-carboxylic acid (38)

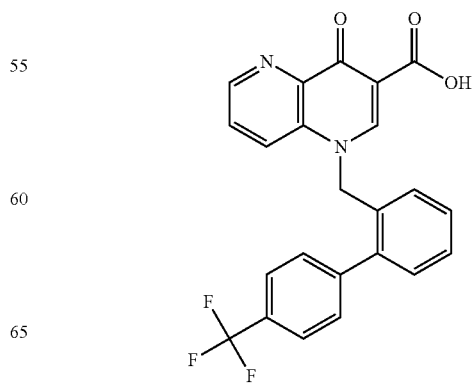

Step 1

3-Chloropicolinoyl chloride (34)

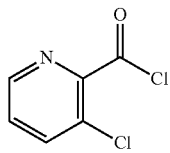

To a suspension of 3-chloropicolinic acid (1.58 g, 10 mmol) in toluene (6 mL) was added an excess of thionyl chloride (9.52 g, 5.84 mL, 80.0 mmol) at room temperature under a nitrogen atmosphere. The resulting suspension was heated to 120° C. (oil bath temperature) and stirred for 20 h. Then, the solvent and excess of thionyl chloride were removed under vacuum and the residue was dissolved one more time in toluene and the solvent was removed again. The resulting residue was dried under high vacuum and used in the next step.

Step 2

(Z)-Ethyl 3-(dimethylamino)-2-(3-chloropicolinoyl) acrylate (35)

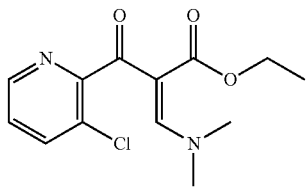 [SMILES: CCOC(=O)/C(=C\N(C)C)C(=O)c1ncccc1Cl]

To a light yellow solution of (E)-ethyl 3-(dimethylamino) acrylate (1.72 g, 12.0 mmol) in toluene (20 mL) was added triethylamine (1.21 g, 1.67 mL, 12.0 mmol) at room temperature. To this, a solution of 3-chloropicolinoyl chloride (34) (1.76 g, 10 mmol) in toluene (5 mL, heated to dissolve) was added. Then, the resulting dark brown solution was heated to 83° C. and stirred for 12 h at this temperature. During this period, it turned to a dark brown solution. Then, the heating was stopped and the dark brown mixture was filtered off and the solids were washed with ethyl acetate. The brown ethyl acetate solution was washed with water which was diluted with 1.0N HCl. The acidic aqueous layer was extracted one more time with ethyl acetate and the combined organic layer was washed with brine solution and dried over anhydrous MgSO$_4$. Filtration and concentration gave only 1.6 g of crude brown mixture. Then, the acidic aqueous layer was extracted with dichloromethane (2×100 mL) and then the aqueous layer was neutralized with a saturated sodium bicarbonate solution and then extracted one more time with dichloromethane. The combined dichloromethane extracts were washed with brine solution and dried over anhydrous MgSO$_4$. Filtration and concentration gave another 1.2 g of dark drown oil which was combined with the first brown residue and the mixture was purified using an ISCO (120 g) column, eluting with ethyl acetate in hexanes (0 to 100%) and then 10% methanol in dichloromethane. The pure fractions were combined and the solvent was removed under vacuum to obtain (Z)-ethyl 3-(dimethylamino)-2-(3-chloropicolinoyl)acrylate (35) (1.16 g, 41% yield) as a dark brown oil.

LC/MS calcd. for C$_{13}$H$_{15}$ClN$_2$O$_3$ (m/e) 282.72, obsd. 283.2 [M+H, ES$^+$].

Step 3

Ethyl 1-(2-bromobenzyl)-4-oxo-1,4-dihydro-1,5-naphthyridine-3-carboxylate (36)

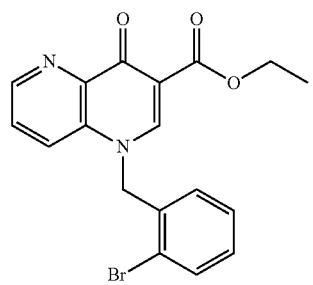 [SMILES: CCOC(=O)c1cn(Cc2ccccc2Br)c2cccnc2c1=O]

To a brown solution of (Z)-ethyl 2-(3-chloropicolinoyl)-3-(dimethylamino)acrylate (35) (850 mg, 3.01 mmol) in DMA (dimethylacetamide) (50 mL) were added a solid powder of tribasic potassium phosphate (1.4 g, 6.61 mmol) and then (2-bromophenyl)methanamine (615 mg, 3.31 mmol) at room temperature under a nitrogen atmosphere. The resulting brown suspension was heated to 74° C. and stirred for 15 h at which time LCMS analysis indicated the absence of starting material. Then, it was cooled to room temperature and poured slowly into water (100 mL). Then, the organic compound was extracted into dichloromethane (2×200 mL). The combined extracts were washed with water, brine solution, and dried over anhydrous MgSO$_4$. Filtration and concentration gave a crude brown oil which was purified using an ISCO (120 g) column, eluting with ethyl acetate in hexanes (0 to 100%) and then 5 to 10% methanol in dichloromethane. The pure fractions were combined and the solvent was removed under vacuum to obtain ethyl 1-(2-bromobenzyl)-4-oxo-1,4-dihydro-1,5-naphthyridine-3-carboxylate (36) (574 mg, 46.8% yield) as a light brown solid.

LC/MS calcd. for C$_{18}$H$_{15}$BrN$_2$O$_3$ (m/e) 387.23, obsd. 389.1 [M+H, ES$^+$].

Step 4

Ethyl 1-oxo-1-((4'-(trifluoromethyl)biphenyl-2-yl)methyl)-1,4-dihydro-1,5-naphthyridine-3-carboxylic acid (37)

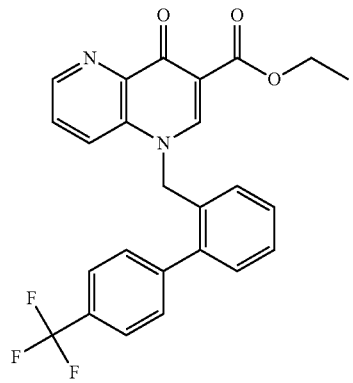 [SMILES: CCOC(=O)c1cn(Cc2ccccc2-c2ccc(C(F)(F)F)cc2)c2cccnc2c1=O]

To a mixture of ethyl 1-(2-bromobenzyl)-4-oxo-1,4-dihydro-1,5-naphthyridine-3-carboxylate (136 mg, 0.35 mmol), 4-(trifluoromethyl)phenylboronic acid (133 mg, 0.7 mmol), palladium(II) acetate (15.7 mg, 0.07 mmol), 2-dicyclohexylphosphino-2',6'-dimethoxybiphenyl (57.5 mg, 0.140 mmol), and tribasic potassium phosphate (371 mg, 1.75 mmol) in a 20 mL vial were added previously degassed toluene (4.5 mL) and water (1.0 mL) at room temperature under a nitrogen atmosphere. The resulting suspension was heated to 100° C. and stirred for 15 h at which time LCMS analysis indicated the absence of starting material. Then, the black reaction mixture was cooled to room temperature and poured into a mixture of water and brine solution and the organic compound was extracted into ethyl acetate (2×100 mL). The combined extracts were washed with brine solution and dried over anhydrous $MgSO_4$. Filtration and concentration gave a crude brown oil which was purified using ISCO (40 g) column chromatography, eluting with ethyl acetate in hexanes (0 to 100%) and 10 to 20% methanol in dichloromethane. The desired fractions were combined and the solvent was removed under vacuum to obtain ethyl 4-oxo-1-((4'-(trifluoromethyl)biphenyl-2-yl)methyl)-1,4-dihydro-1,5-naphthyridine-3-carboxylate (37) (12 mg, 7.6% yield) as a brown solid.

LC/MS calcd. for $C_{25}H_{19}F_3N_2O_3$ (m/e) 452.43, obsd. 453.2 [M+H, $ES^+$].

Step 5

1-Oxo-1-((4'-(trifluoromethyl)biphenyl-2-yl)methyl)-1,4-dihydro-1,5-naphthyridine-3-carboxylic acid (38)

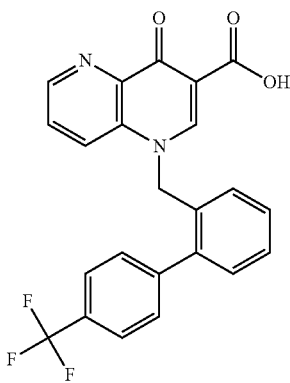 [SMILES: O=C(O)c1cn(Cc2ccccc2-c2ccc(C(F)(F)F)cc2)c2cccnc2c1=O]

To a solution of ethyl 4-oxo-1-((4'-(trifluoromethyl)biphenyl-2-yl)methyl)-1,4-dihydro-1,5-naphthyridine-3-carboxylate (37) (11 mg, 0.024 mmol) in dimethyl sulfoxide (1 mL) and methanol (5 mL) was added the solid lithium hydroxide monohydrate (51.0 mg, 1.22 mmol) at room temperature under a nitrogen atmosphere. It gave a clear solution within 30 minutes and this light yellow solution was stirred for 15 h at which time LCMS analysis indicated the absence of starting material. Then, the mixture was diluted with water and the methanol was removed under vacuum. The basic aqueous layer was diluted with water and then neutralized with 1.0N HCl. The resulting acid was extracted with ethyl acetate (2×30 mL) and the combined extracts were washed with brine solution and dried over anhydrous $MgSO_4$. Filtration and concentration gave a brown residue which was dissolved in acetonitrile and water. It was frozen and then lyophilized under high vacuum to obtain 4-oxo-1-((4'-(trifluoromethyl) biphenyl-2-yl)methyl)-1,4-dihydro-1,5-naphthyridine-3-carboxylic acid (38) (4.4 mg, 42.6% yield) as a light yellow solid.

$^1$H NMR (DMSO-$d_6$) δ: 12.8 (br. s., 1H), 8.96 (s, 1H), 8.89 (d, J=6.0 Hz, 1H), 7.95 (d, J=8 Hz, 1H), 7.75-7.8 (m, 2H), 7.58 (d, J=8 Hz, 1H), 7.3-7.48 (m, 5H), 7.15 (d, J=8 Hz, 1H), 5.85 (s, 2H).

LC/MS calcd. for $C_{23}H_{16}F_3N_2O_3$ (m/e) 424.37, obsd. 425.1 [M+H, $ES^+$].

The invention claimed is:
1. A compound having the formula (V),

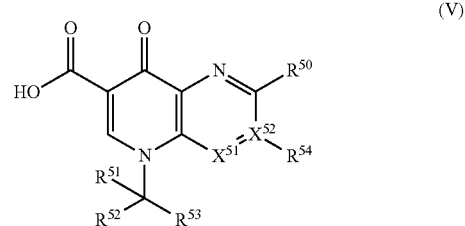

(V)

wherein $X^{51}$ is CH;

$X^{52}$—$R^{54}$ is C—$R^{57}$;

$X^{53}$ is $NR^{55}$, $N(R^{55})C(O)$, $C(O)NR^{55}$, O, C(O), C(O)O, OC(O), $N(R^{55})SO_2$, $SO_2N(R^{55})$, S, SO, or $SO_2$;

$R^{50}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl -(optionally substituted aryl);

$R^{51}$ is —H, a —$C_{1-6}$ alkyl group, or a —$C_{1-6}$ alkyl group which is substituted by one or more halogen atoms;

$R^{52}$ is —H, a —$C_{1-6}$ alkyl group, or a —$C_{1-6}$ alkyl group which is substituted by one or more halogen atoms;

or wherein $R^{51}$ and $R^{52}$ can be joined together to form a 3- to 7-membered carbocyclic or heterocyclic ring;

$R^{53}$ is —$R^{56}$, or —$X^{53}$—$R^{56}$;

$R^{55}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl);

$R^{56}$ is -(optionally substituted hydrocarbon group which contains from 5 to 20 carbon atoms and optionally 1 to 4 heteroatoms selected from O, N and S and which contains at least one ring);

$R^{57}$ is —H, —Hal or —$C_{1-6}$ alkyl;

$R^{58}$ is —H, —$C_{1-6}$ alkyl, or —$(CH_2CH_2O)_rH$;

$R^{59}$ is —H, or —$C_{1-6}$ alkyl;

R is independently selected from —$C_{1-6}$ alkyl, —C(O)—$C_{1-4}$ alkyl, —Hal, —$CF_3$, —CN, —$COOR^{58}$, —$OR^{58}$, —$(CH_2)_qNR^{58}R^{59}$, —C(O)—$NR^{58}R^{59}$, and —$NR^{58}$—C(O)—$C_{1-6}$ alkyl;

q is 0, 1, 2, 3 or 4; and r is 1, 2 or 3;

wherein the alkyl group, aryl group, hydrocarbon group and/or cycloalkyl group can be optionally substituted with one or more substituents R, or a pharmaceutically acceptable salt, tautomer, racemate, enantiomer, or diastereomer or mixture thereof
with the proviso that the compound is not:

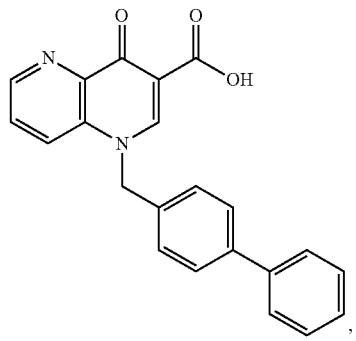
,

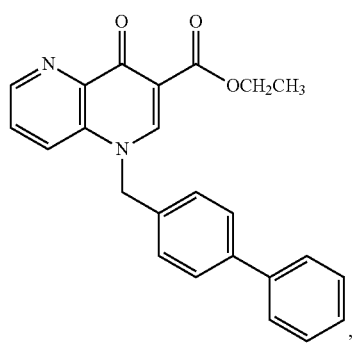
,

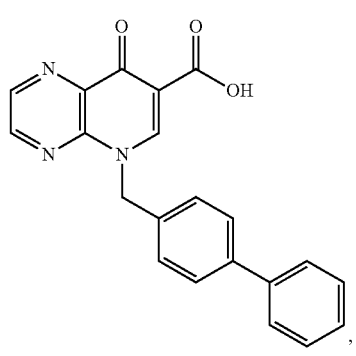
, lp;lp

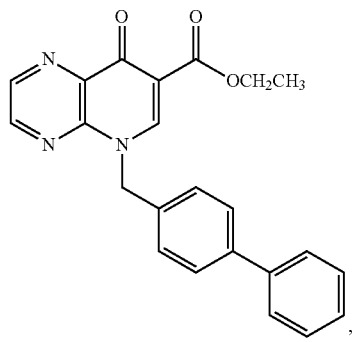
, or
ethyl 4-oxo-1-{[4-(1H-pyrazolo-1-yl)phenyl]methyl}-1,4-dihydro-1,5-naphthyridine-3-carboxylate.

2. The compound according to claim 1, wherein $R^{53}$ is $-R^{56}$.

3. The compound according to claim 1, wherein $R^{53}$ is $-X^{53}-R^{56}$ and $X^{53}$ is $N(R^{55})SO_2$.

4. The compound according to claim 1, wherein $R^{51}$ and $R^{52}$ are $-H$.

5. The compound according to claim 1, wherein $R^{50}$ is $-H$, or -(optionally substituted $C_{1-6}$ alkyl).

6. The compound according to claim 1, wherein $R^{56}$ is selected from the group consisting of

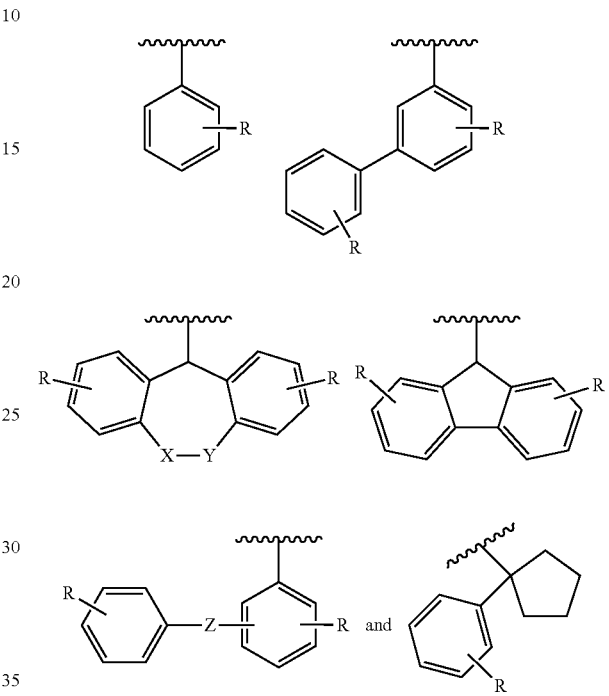

wherein
X is absent, $CH_2$, NH, C(O)NH, S or O;
Y is $CH_2$;
Z is O or S; and
R is independently selected from $-H$, $-C_{1-6}$ alkyl, $-CF_3$, -halogen, $-CN$, $-OH$, and $-O-C_{1-6}$ alkyl.

7. A pharmaceutical composition comprising:
a compound having the formula (V);

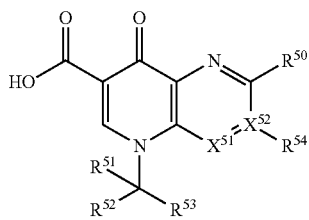

(V)

wherein
$X^{51}$ is CH;
$X^{52}-R^{54}$ is $C-R^{57}$;
$X^{53}$ is $NR^{55}$, $N(R^{55})C(O)$, $C(O)NR^{55}$, O, C(O), C(O)O, OC(O), $N(R^{55})SO_2$, $SO_2N(R^{55})$, S, SO, or $SO_2$;
$R^{50}$ is $-H$, -(optionally substituted $C_{1-6}$ alkyl), -(optionally substituted $C_{3-7}$ cycloalkyl), -(optionally substituted aryl), $-C_{1-4}$ alkyl-(optionally substituted $C_{3-7}$ cycloalkyl), or $-C_{1-4}$ alkyl-(optionally substituted aryl);

$R^{51}$ is —H, a —$C_{1-6}$ alkyl group, or a —$C_{1-6}$ alkyl group which is substituted by one or more halogen atoms;

$R^{52}$ is —H, a —$C_{1-6}$ alkyl group, or a —$C_{1-6}$ alkyl group which is substituted by one or more halogen atoms; or wherein $R^{51}$ and $R^{52}$ can be joined together to form a 3- to 7-membered carbocyclic or heterocyclic ring;

$R^{53}$ is —$R^{56}$, or —$X^{53}$—$R^{56}$;

$R^{55}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl);

$R^{56}$ is -(optionally substituted hydrocarbon group which contains from 5 to 20 carbon atoms and optionally 1 to 4 heteroatoms selected from O, N and S and which contains at least one ring);

$R^{57}$ is —H, —Hal or —$C_{1-6}$ alkyl;

$R^{58}$ is —H, —$C_{1-6}$ alkyl, or —$(CH_2CH_2O)_rH$;

$R^{59}$ is —H, or —$C_{1-6}$ alkyl;

R is independently selected from —$C_{1-6}$ alkyl, —$C(O)$—$C_{1-6}$ alkyl, —Hal, —$CF_3$, —CN, —$COOR^{58}$, —$OR^{58}$, —$(CH_2)_qNR^{58}R^{59}$, —$C(O)$—$NR^{58}R^{59}$, and —$NR^{58}$—$C(O)$—$C_{1-6}$ alkyl;

q is 0, 1, 2, 3 or 4; and r is 1, 2 or 3;

wherein the alkyl group, aryl group, hydrocarbon group and/or cycloalkyl group can be optionally substituted with one or more substituents R, or a pharmaceutically acceptable salt, tautomer, racemate, enantiomer, or diastereomer or mixture thereof and one or more pharmaceutically acceptable excipient(s) and/or carrier(s);

with the proviso that the compound is not:

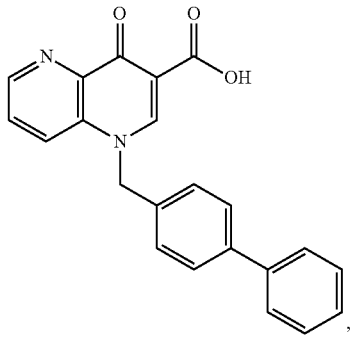

,

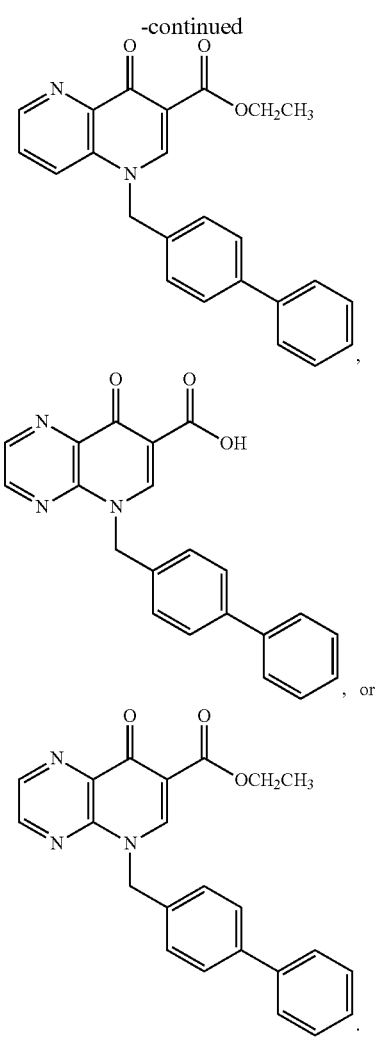

8. The pharmaceutical composition according to claim 7, further comprising a further medicament selected from the group consisting of a polymerase inhibitor which is different from the compound having the formula (V); a neuramidase inhibitor; a M2 channel inhibitor; an alpha glucosidase inhibitor; a ligand of another influenza target; an antibiotic, an anti-inflammatory agent, a lipoxygenase inhibitor, an EP ligand, a bradykinin ligand, and a cannabinoid ligand, and combinations thereof.

* * * * *